(12) United States Patent
Su et al.

(10) Patent No.: US 9,089,699 B2
(45) Date of Patent: Jul. 28, 2015

(54) ADAPTIVE STIMULATION FOR TREATING URGENCY OR INCONTINENCE

(75) Inventors: Xin Su, Plymouth, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/701,690

(22) PCT Filed: Jun. 6, 2011

(86) PCT No.: PCT/US2011/039322
§ 371 (c)(1),
(2), (4) Date: Dec. 3, 2012

(87) PCT Pub. No.: WO2011/156288
PCT Pub. Date: Dec. 15, 2011

(65) Prior Publication Data
US 2013/0079841 A1  Mar. 28, 2013

Related U.S. Application Data

(60) Provisional application No. 61/352,172, filed on Jun. 7, 2010.

(51) Int. Cl.
*A61N 1/36* (2006.01)
(52) U.S. Cl.
CPC .................................. *A61N 1/36007* (2013.01)
(58) Field of Classification Search
USPC .......................................................... 607/41
See application file for complete search history.

(56) References Cited

U.S. PATENT DOCUMENTS

| 4,406,288 A * | 9/1983 | Horwinski et al. ............. 607/41 |
| 5,919,216 A | 7/1999 | Houben et al. |
| 5,984,854 A * | 11/1999 | Ishikawa et al. .................. 600/9 |
| 6,141,587 A * | 10/2000 | Mower .............................. 607/9 |
| 6,393,323 B1 * | 5/2002 | Sawan et al. .................... 607/41 |
| 7,689,276 B2 | 3/2010 | Dobak |
| 2003/0100930 A1 | 5/2003 | Cohen et al. |

(Continued)

FOREIGN PATENT DOCUMENTS

| WO | 2006092007 A1 | 9/2006 |
| WO | 2009045297 A1 | 4/2009 |
| WO | WO2010/123704 | 10/2010 |

OTHER PUBLICATIONS

PCT/US11/039322: Search Report and Written Opinion.

(Continued)

*Primary Examiner* — Carl H Layno
*Assistant Examiner* — Erin Piateski
(74) *Attorney, Agent, or Firm* — Shumaker & Sieffert, P.A.

(57) ABSTRACT

In one example, a system includes a therapy module and a processor. The processor detects a voiding event of a patient and controls the therapy module to deliver electrical stimulation to the patient at a first intensity level for a period of time in response to the detection of the voiding event. Immediately following the period of time, the processor controls the therapy module to increase intensity of the electrical stimulation from the first intensity level to a second intensity level before a subsequent voiding event of the patient by at least controlling the therapy module to deliver stimulation to the patient at a plurality of intermediate intensity levels between the first and second intensity levels prior to delivering stimulation to the patient at the second intensity level following the detection of the voiding event.

44 Claims, 17 Drawing Sheets

(56) References Cited

U.S. PATENT DOCUMENTS

| | | | |
|---|---|---|---|
| 2004/0162594 A1* | 8/2004 | King | 607/40 |
| 2005/0065575 A1 | 3/2005 | Dobak | |
| 2006/0074450 A1* | 4/2006 | Boveja et al. | 607/2 |
| 2006/0122660 A1 | 6/2006 | Boveja et al. | |
| 2006/0161218 A1 | 7/2006 | Danilov | |
| 2006/0200205 A1* | 9/2006 | Haller | 607/41 |
| 2007/0100387 A1* | 5/2007 | Gerber | 607/41 |
| 2007/0100388 A1 | 5/2007 | Gerber | |
| 2009/0054950 A1* | 2/2009 | Stephens | 607/41 |
| 2009/0118777 A1 | 5/2009 | Iki et al. | |
| 2009/0131993 A1 | 5/2009 | Rousso et al. | |
| 2009/0138061 A1* | 5/2009 | Stephens et al. | 607/41 |
| 2009/0264955 A1* | 10/2009 | Giftakis et al. | 607/45 |
| 2009/0264956 A1* | 10/2009 | Rise et al. | 607/45 |
| 2009/0264957 A1* | 10/2009 | Giftakis et al. | 607/45 |
| 2009/0264967 A1* | 10/2009 | Giftakis et al. | 607/62 |
| 2009/0306460 A1* | 12/2009 | Stephens et al. | 600/30 |
| 2010/0076254 A1* | 3/2010 | Jimenez et al. | 600/30 |

OTHER PUBLICATIONS

International Preliminary Report on Patentability from international application No. PCT/US2011/039322, dated Dec. 10, 2012, 11 pp.

Office Action from U.S. Appl. No. 13/701,603 dated Oct. 30, 2013, 11 pp.

Response to Office Action dated Apr. 16, 2014, from U.S. Appl. No. 13/701,603, filed Jun. 16, 2014, 15 pp.

Notice of Appeal from U.S. Appl. No. 13/701,603, filed Jul. 16, 2014, 1 pp.

Pre-Appeal Brief Request for Review from U.S. Appl. No. 13/701,603, filed Jul. 16, 2014, 6 pp.

Final Office Action from U.S. Appl. No. 13/701,603, dated Apr. 16, 2014, 13 pp.

Notice of Allowance from U.S. Appl. No. 13/701,603, dated Oct. 24, 2014, 7 pp.

\* cited by examiner

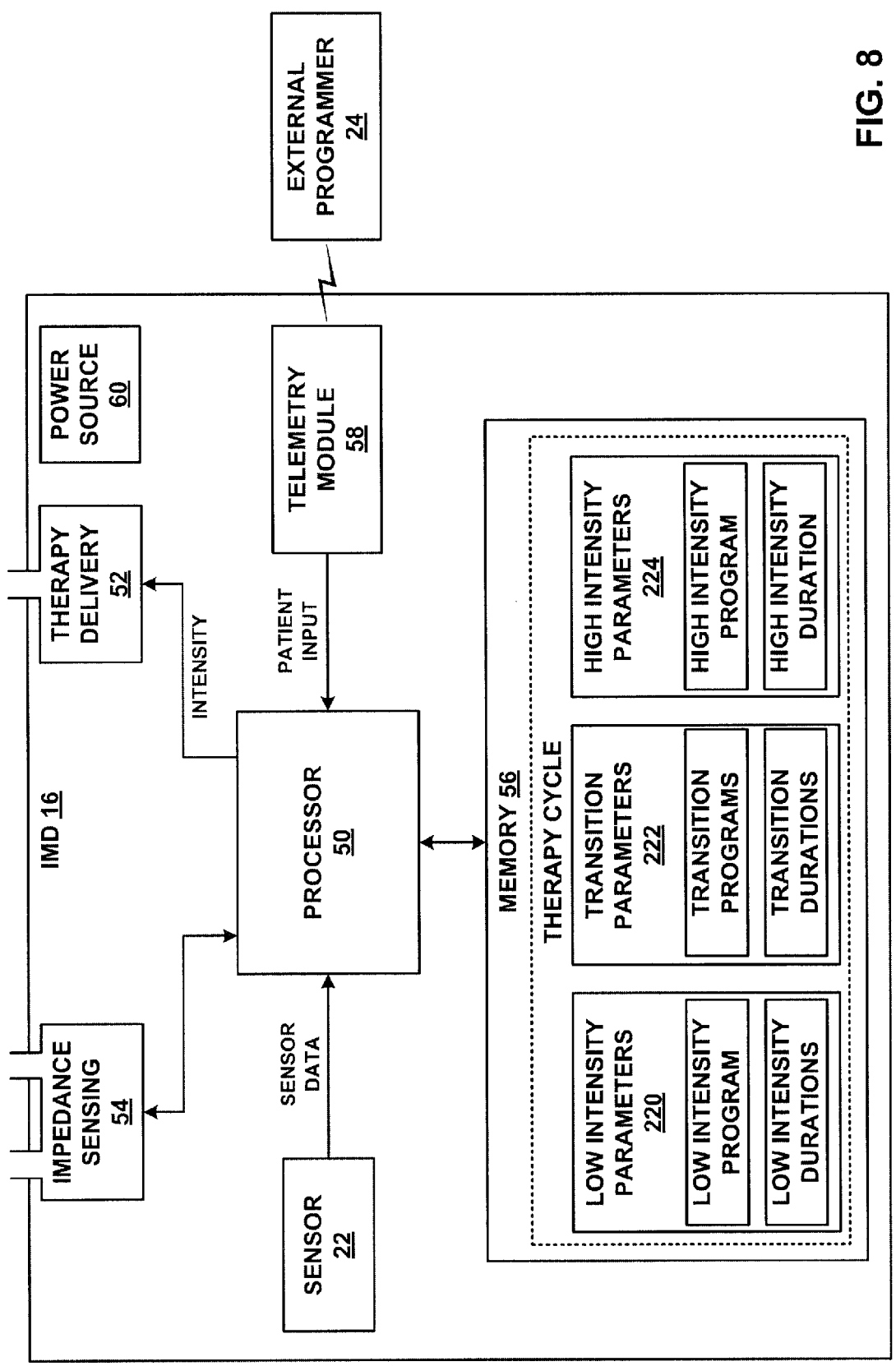

ADAPTIVE STIMULATION FOR TREATING URGENCY OR INCONTINENCE

TECHNICAL FIELD

The disclosure relates to medical devices and, more particularly, to medical devices that may be configured to treat urgency and/or incontinence.

BACKGROUND

Urgency and urinary incontinence (e.g., an inability to control urinary function) are problems that afflict people of all ages, genders, and races. Various muscles, nerves, organs and conduits within the pelvic floor cooperate to collect, store and release urine. A variety of disorders may compromise urinary tract performance, and contribute to urgency or incontinence. Many of the disorders may be associated with aging, injury, or illness.

Urgency may originate from disorders of portions of the peripheral or central nervous system which control the bladder micturition reflex. Nerve disorders may also lead to overactive bladder activities and/or may prevent proper triggering and operation of the bladder. Furthermore, urgency or urinary incontinence may also result from improper communication between the nervous system and the urethra.

SUMMARY

Devices, systems, and techniques for managing urgency or urinary incontinence of a patient using electrical stimulation are described. In some examples, a medical device is configured to deliver a relatively low intensity electrical stimulation to a patient for a period of time and then gradually increase the intensity of electrical stimulation from the relatively low intensity level to a higher intensity level, such that stimulation is delivered at a plurality of intermediate intensity levels between the relatively low and high intensity levels. In some examples, the medical device is configured to deliver the low intensity electrical stimulation to the patient immediately after a voiding event and then gradually increase the intensity of electrical stimulation to a predetermined higher intensity level as time passes since the voiding event and prior to a subsequent voiding event. In this way, stimulation intensity is increased between voiding events. After a subsequent voiding event of the patient occurs, the medical device may decrease the intensity of stimulation to the relatively low intensity level and subsequently gradually increase the stimulation intensity to the predetermined higher intensity level.

In some examples, the relatively low intensity stimulation is selected such that delivery of stimulation to the patient at the relatively low intensity level may result in a reduction in bladder contraction frequency of the patient that manifests a period of time after application of the relatively low intensity stimulation. In other words, the relatively low intensity stimulation may elicit a reduction in bladder contraction frequency by the patient that is delayed (e.g., a delayed physiological response) relative to the time the relatively low intensity stimulation is applied or initiated.

The higher intensity stimulation may elicit a physiological response from the patient that is different than the delayed response generated by delivery of stimulation according to the relatively low intensity stimulation. In some examples, the higher intensity stimulation is selected such that delivery of stimulation to the patient at the higher intensity level may generate an immediate reduction in bladder contraction frequency, rather than a delayed response as with the relatively low intensity stimulation. In general, the higher intensity stimulation may produce a relatively strong bladder inhibition that attenuates a strong urgency sensation in the patient when the patient's bladder holds an amount of urine, while the relatively low intensity stimulation may produce relatively less bladder inhibition, which may be effective in reducing the sensation of urgency felt by the patient when the bladder holds a lesser amount of urine and the patient's sensation is not as strong.

In one example, the disclosure is directed to a method comprising detecting a voiding event of a patient and delivering electrical stimulation to the patient at a first intensity level for a period of time in response to the detection of the voiding event. The method further comprises, immediately following the period of time, increasing intensity of the electrical stimulation from the first intensity level to a second intensity level before a subsequent voiding event of the patient. Increasing intensity of the electrical stimulation comprises delivering electrical stimulation to the patient at a plurality of intermediate intensity levels between the first and second intensity levels prior to delivering stimulation to the patient at the second intensity level following the detection of the voiding event.

In another example, the disclosure is directed to a system comprising a therapy module and a processor. The processor detects a voiding event of a patient and controls the therapy module to deliver electrical stimulation to the patient at a first intensity level for a period of time in response to the detection of the voiding event. Immediately following the period of time, the processor controls the therapy module to increase intensity of the electrical stimulation from the first intensity level to a second intensity level before a subsequent voiding event of the patient by at least controlling the therapy module to deliver stimulation to the patient at a plurality of intermediate intensity levels between the first and second intensity levels prior to delivering stimulation to the patient at the second intensity level following the detection of the voiding event.

In another example, the disclosure is directed to a system comprising means for detecting a voiding event of a patient and means for delivering electrical stimulation to the patient at a first intensity level for a period of time in response to the detection of the voiding event. The system further comprises means for increasing intensity of the electrical stimulation from the first intensity level to a second intensity level immediately following the period of time and before a subsequent voiding event of the patient. The means for increasing intensity of the electrical stimulation comprises at least delivering electrical stimulation to the patient at a plurality of intermediate intensity levels between the first and second intensity levels prior to delivering stimulation to the patient at the second intensity level following the detection of the voiding event.

In another example, the disclosure is directed to a computer-readable storage medium comprising instructions that cause a programmable processor to detect a voiding event of a patient and deliver electrical stimulation to the patient at a first intensity level for a period of time in response to the detection of the voiding event. Additionally, the computer-readable storage medium comprises instructions that cause the programmable processor to increase intensity of the electrical stimulation from the first intensity level to a second intensity level immediately following the period of time and before a subsequent voiding event of the patient. Increasing intensity of the electrical stimulation comprises delivering electrical stimulation to the patient at a plurality of intermediate intensity levels between the first and second intensity levels prior to delivering stimulation to the patient at the second intensity level following the detection of the voiding event.

In still other examples, the disclosure is directed to a method comprising delivering electrical stimulation therapy to a patient to manage at least one of urinary urgency or urinary incontinence of the patient according to a plurality of repeating therapy cycles, each therapy cycle comprising, during a predetermined period of time, delivering electrical stimulation to the patient according to a first electrical stimulation intensity level. Each therapy cycle further comprises delivering electrical stimulation to the patient according to a plurality of intermediate intensity levels between the first intensity level and a second intensity level, wherein each intermediate intensity level has a greater intensity than a previous intermediate intensity level. Additionally, each therapy cycle comprises delivering electrical stimulation to the patient according to the second electrical stimulation intensity level.

In another example, the disclosure is directed to a system comprising a therapy module and a processor. The processor controls the therapy module to deliver electrical stimulation therapy to a patient to manage at least one of urinary urgency or urinary incontinence of the patient according to a plurality of repeating therapy cycles. The processor controls the therapy module during each therapy cycle to, during a predetermined period of time, deliver electrical stimulation to the patient according to a first electrical stimulation intensity level. The processor also controls the therapy module during each therapy cycle to, during the predetermined period of time, deliver electrical stimulation to the patient according to a plurality of intermediate intensity levels between the first intensity level and a second intensity level. Each intermediate intensity level has a greater intensity than a previous intermediate intensity level. Additionally, the processor controls the therapy module during each therapy cycle to, during the predetermined period of time, deliver electrical stimulation to the patient according to the second electrical stimulation intensity level.

In another example, the disclosure is directed to a system comprising means for delivering electrical stimulation therapy to a patient to manage at least one of urinary urgency or urinary incontinence of the patient according to a plurality of repeating therapy cycles. Each therapy cycle comprises, during a predetermined period of time, means for delivering electrical stimulation to the patient according to a first electrical stimulation intensity level and means for delivering electrical stimulation to the patient according to a plurality of intermediate intensity levels between the first intensity level and a second intensity level. Each intermediate intensity level has a greater intensity than a previous intermediate intensity level. Each therapy cycle further comprises, during the predetermined period of time, means for delivering electrical stimulation to the patient according to the second electrical stimulation intensity level.

In another example, the disclosure is directed to a computer-readable storage medium comprising instructions that cause a programmable processor to deliver electrical stimulation therapy to a patient to manage at least one of urinary urgency or urinary incontinence of the patient according to a plurality of repeating therapy cycles. Each therapy cycle comprises, during a predetermined period of time delivering electrical stimulation to the patient according to a first electrical stimulation intensity level and delivering electrical stimulation to the patient according to a plurality of intermediate intensity levels between the first intensity level and a second intensity level. Each intermediate intensity level has a greater intensity than a previous intermediate intensity level. Each therapy cycle further comprises delivering electrical stimulation to the patient according to the second electrical stimulation intensity level.

In another example, the disclosure is directed to an article of manufacture that includes a computer-readable storage medium. The computer-readable storage medium includes computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable medium may be non-transitory.

The details of one or more aspects of the disclosure are set forth in the accompanying drawings and the description below.

BRIEF DESCRIPTION OF DRAWINGS

FIG. 8 is a functional block diagram of an example IMD configured to transition between a low intensity stimulation and a high intensity stimulation.

DETAILED DESCRIPTION

Figure 1:
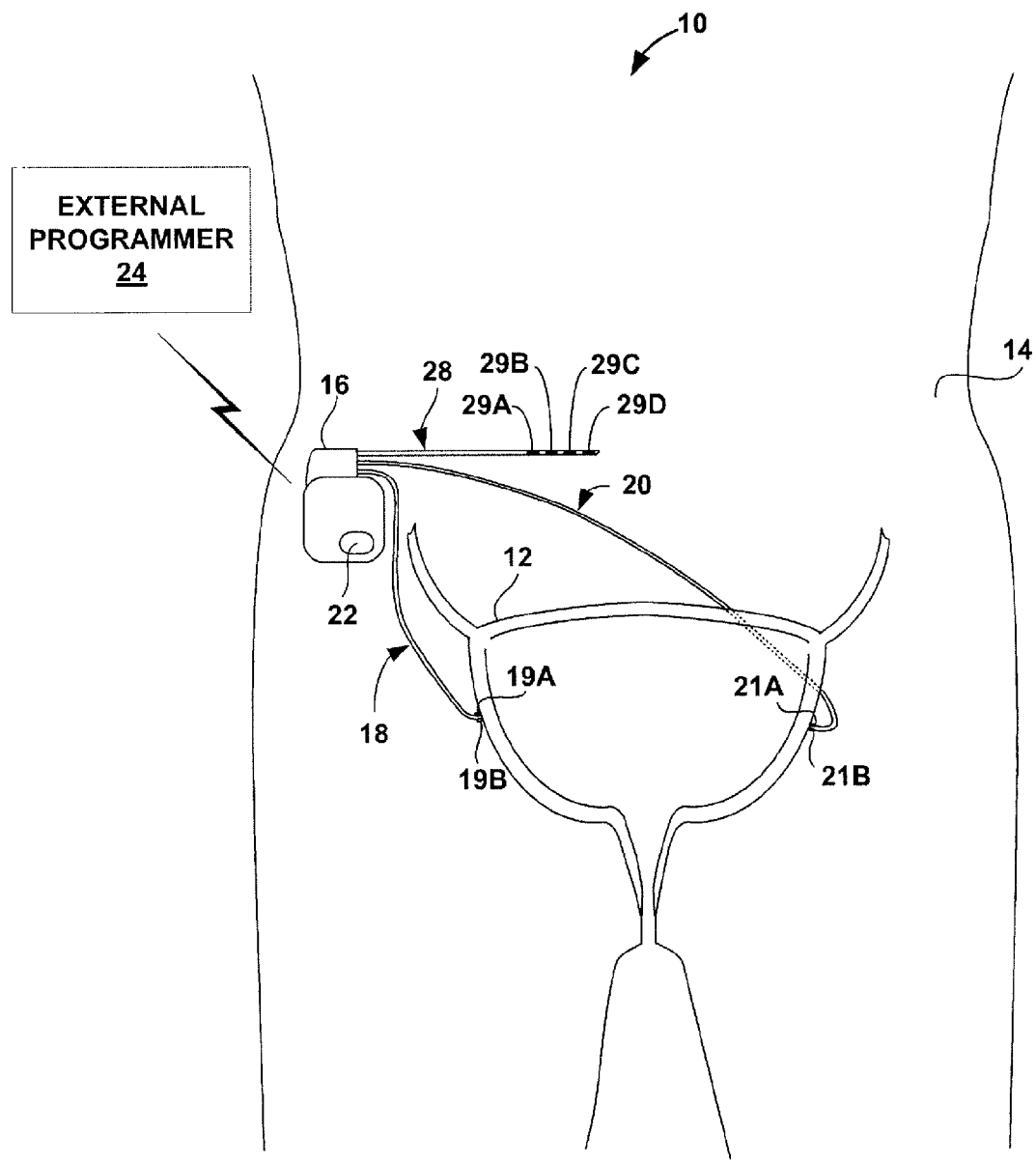
FIG. 1 is a conceptual diagram illustrating an example therapy system that delivers stimulation therapy to a patient to manage urgency and urinary incontinence.

As used in this disclosure, "urinary urgency" or "urgency" may refer to a patient's sudden, compelling urge to urinate. In some cases, urinary urgency may be associated with nerve disorders that cause an involuntary loss of urine (e.g., urge incontinence). Electrical stimulation therapy may be used to treat urgency and/or urinary incontinence. Electrical stimulation therapy may include delivery of electrical stimulation from a medical device (e.g., an implantable medical device (IMD)) to a tissue site proximate a nerve in the pelvic floor of a patient, such as the sacral nerve, pudendal nerve, dorsal genital nerve, or branches of any of the aforementioned nerves. Electrical stimulation of the sacral nerve may modulate afferent nerve activities to restore urinary function. In addition, electrical stimulation of the nerves innervating pelvic floor muscles may strengthen pelvic floor muscle and promote urinary continence. Although the present disclosure describes application of electrical stimulation using an IMD, the devices, systems, and techniques of the present disclosure may also be implemented in an external medical device that applies electrical stimulation via implanted or external electrodes.

In accordance with some techniques described herein, an IMD generates and delivers a relatively low intensity stimulation (lower in intensity than the higher intensity stimulation described below) that is selected such that delivery of stimulation to the patient at the relatively low intensity level may result in a reduction in bladder contraction frequency of the patient that manifests a period of time after application of the low intensity stimulation or after initiation of the low intensity stimulation. In other words, the low intensity stimulation produces a reduction in bladder contraction frequency that is delayed (e.g., a delayed physiological response) relative to the time the low intensity stimulation is applied and/or initiated. The relatively low intensity stimulation is also referred to herein as "low intensity stimulation."

The IMD may also generate and deliver a higher intensity stimulation that may elicit a physiological response that is different than the delayed response generated by delivery of stimulation according to the low intensity stimulation. The higher intensity stimulation has a higher intensity than the low intensity stimulation, and is also referred to herein as "high intensity stimulation." In some examples, the high intensity stimulation is selected such that delivery of stimulation to the patient at the high intensity level may result in a substantially immediate or immediate (commonly referred to herein as "immediate") reduction in bladder contraction frequency, rather than a delayed response as with the low intensity stimulation. The substantially immediate reduction in bladder contraction frequency or other physiological response elicited by the high intensity stimulation may occur substantially faster than the delayed response elicited by the delivery of the low intensity stimulation to the patient. Thus, the physiological response resulting from the delivery of the high intensity stimulation may be referred to as an acute physiological response. In some examples, the acute physiological response occurs within about 0.1 seconds to about 30 seconds after the high intensity stimulation is delivered to the patient.

In one example, the IMD may deliver a relatively low intensity stimulation to the tissue site for a period of time and then deactivate the delivery of stimulation (e.g., such that substantially no or a negligible amount of therapy is delivered). In this example, the patient may exhibit a reduction in bladder contraction frequency during the period of time in which the low intensity stimulation is delivered to the patient, and after the period of time, the patient may exhibit a greater reduction in bladder contraction frequency. After a period of time following removal of the low intensity stimulation, the reduction in bladder contraction frequency may dissipate and bladder contraction frequency may be allowed to increase. In other examples, low intensity stimulation may not be terminated prior to the pronounced reduction in contraction frequency, but, instead, may be continuously delivered to the patient, such that stimulation is delivered to the patient while the reduction in bladder contraction frequency is manifested.

Throughout the disclosure, the term "intensity" is used to describe a level of electrical stimulation delivered to a patient. An intensity of stimulation may be a function of, for example, a current or voltage amplitude of the stimulation signal, the frequency of the stimulation signal, the shape of the stimulation signal, the duty cycle of the stimulation signal, the electrode combination used to deliver the stimulation signal, or any combination of the stimulation parameters. Thus, in some examples, intensity of stimulation may be modulated by modifying an amplitude of the electrical stimulation applied to the patient. Amplitude of electrical stimulation may refer to a magnitude of the voltage and/or current of a stimulation signal applied to the patient by the IMD. For example, the IMD may increase/decrease a voltage and/or current delivered to the patient to increase/decrease the intensity of the electrical stimulation. A voltage/current amplitude delivered to the patient that is less than a threshold voltage/current (e.g., a low intensity) may elicit the delayed physiological response by the patient, while a voltage/current delivered to the patient that is greater than the threshold voltage/current (e.g., a high intensity) may not elicit the delayed physiological response (e.g., elicit an immediate physiological response). For example only, a voltage amplitude delivered to the patient may include a range of voltages from about 0.001V to about 50V.

Alternatively, or additionally, in examples in which the IMD generates and delivers stimulation pulses, the IMD may vary the pulse rate and/or pulse width of the delivered stimulation to modulate the intensity of stimulation, e.g., selectively elicit the delayed physiological response and the immediate physiological response. In examples described herein, the pulse rate of stimulation may refer to the number of times per second that a pulse is delivered, measured in pulses per second or Hertz (Hz). For example only, pulse rate may include a range of rates from about 0.1 Hz to about 30 Hz. The pulse width may refer to the duration of the stimulation pulse delivered, measured in microseconds (μs) for example. For example only, pulse width may include a range of pulse widths from about 10 μs to 5000 μs.

In some examples, pulse rates that elicit the delayed and immediate physiological responses may not be defined based on a relative magnitude of the pulse rate relative to a threshold pulse rate. Instead, certain pulse rates or ranges of pulse rates may elicit the delayed physiological response, while other certain pulse rates or ranges of pulse rates may produce a response other than the delayed response (e.g., the immediate response). Accordingly, the IMD may selectively set the pulse rate of electrical stimulation delivered to the patient in order to produce a desired response. A low intensity of electrical stimulation in terms of pulse rate may be defined based on the physiological response produced by the specific pulse rate. For example, electrical stimulation including pulse rates or ranges of pulse rates that produce the delayed response may be referred to as low intensity stimulation, while pulse rates or ranges of pulse rates that produce an immediate response may be referred to as high intensity stimulation. In some examples, low intensity stimulation may include frequency or pulse rates of approximately 0.1 Hz to approximately 5 Hz (e.g., approximately 1 Hz), while high intensity stimulation may include pulse rates from approximately 5 Hz to 20 Hz (e.g., approximately 10 Hz).

In a similar manner, pulse widths that elicit the delayed and immediate physiological responses may not be defined based on a relative magnitude of the pulse width relative to a threshold pulse width. Instead, certain pulse widths or ranges of pulse widths may elicit the delayed physiological response, while other certain pulse widths or ranges of pulse widths may elicit a physiological response other than the delayed response (e.g., the immediate response). Accordingly, the IMD may selectively set the pulse width of electrical stimulation delivered to the patient in order to produce a desired physiological response. In some examples, a low intensity of electrical stimulation in terms of pulse width may be defined based on the physiological response produced by the specific pulse width. For example, electrical stimulation including pulse widths or ranges of pulse widths that produce the delayed response may be referred to as low intensity stimulation, while pulse widths or ranges of pulse widths that produce an immediate response may be referred to as high intensity stimulation.

Although the IMD is described above as adjusting one of the amplitude, pulse rate, or pulse width to adjust the intensity of stimulation, the IMD may also adjust intensity of stimulation by adjusting the frequency of the stimulation signal, the shape of the stimulation signal, the duty cycle of the stimulation signal, the electrode combination or any combination of the aforementioned stimulation parameters or other stimulation parameters. Although electrical stimulation is described above as including discrete pulses, in some examples, the IMD may deliver electrical stimulation using a continuous waveform.

In some examples, the low intensity level and the high intensity level may be defined relative to a threshold intensity. For example, a low intensity level may be a level of intensity that is less than or equal to the threshold intensity, while a high intensity level may be a level of intensity that is greater than the threshold intensity. In examples in which the low intensity level and the high intensity level are defined relative to the threshold intensity, the low intensity level may be referred to as a "subthreshold intensity." For example, the subthreshold intensity may be a fraction of the threshold intensity (e.g., 20% of the threshold), while the high intensity may be a multiple of the threshold intensity (e.g., twice the threshold intensity). In some examples, the low intensity stimulation (e.g., subthreshold intensity) may not be perceived by the patient, while the high threshold stimulation may be perceived by the patient (e.g., as paresthesia).

In some examples, the threshold stimulation intensity may be defined as the stimulation intensity at which a substantially acute, physiologically significant response of the patient is first observed when increasing the stimulation intensity from a low intensity to a higher intensity. Stated another way, the threshold intensity may be defined as approximately the lowest stimulation intensity that elicits an acute, physiologically significant response of the patient. In some examples, the physiological response may be different than that elicited by the delivery of the low intensity stimulation. In some examples, an acute response may be defined as a physiological response that occurs immediately (e.g., within about 30 seconds or less, such as about 10 seconds from the initiation of the stimulation delivery at the particular intensity level) when the patient receives the stimulation.

The acute physiological response that is used to determine the threshold may be manifest in a number of different examples. For example, the acute physiological response may be a motor response, a stimulation perception response, or a detected physiological response, such as a nerve action potential. A stimulation perception response may be observed and reported by the patient, e.g., as a paresthesia or other sensation. However, a motor response or a physiological response (e.g., a nerve impulse or non-therapeutic effect) may be reported by the patient, observed by a clinician, or automatically detected by one or more sensors internal or external to the patient. In some examples, whether a response is physiologically significant may be defined by the patient. For example, the stimulation may elicit movement of a toe of the patient, and the patient may define the movement of the toe as physiologically significant when the movement of the toe is perceptible or when the movement of the toe is above some arbitrary amount defined by the patient or the clinician.

The threshold intensity may be determined experimentally for each patient. An iterative stimulation procedure may be used to determine the threshold intensity. The iterative procedure may be performed by a clinician, for example, using the IMD implanted in the patient, or another device, or automatically by the IMD. In one example, a clinician may begin the determination of the threshold intensity level with a stimulation intensity that is not likely to produce any acute physiologically significant response. This intensity may be selected, for example, based on the clinician's knowledge in some cases. The clinician can select the initial intensity by, for example, setting stimulation parameters (e.g., a current amplitude, a voltage amplitude, a frequency or pulse rate, a shape, a pulse width, a duty cycle, and/or the combination of electrodes) to produce a relatively low stimulation intensity and controlling the IMD to deliver stimulation to the patient using these parameters. Then, the clinician may incrementally increase one or more stimulation parameters, e.g., a current amplitude, pulse width, or pulse frequency, until an acute physiological response to the stimulation is detected. Once an acute physiological response is detected, the stimulation parameter may define the threshold intensity.

For example, if no physiological response is observed in response to the initial intensity level, a value of one stimulation parameter may then be changed to increase the stimulation intensity while the remaining parameters are kept approximately constant, and the IMD may be controlled to deliver stimulation at the new stimulation intensity. The stimulation parameter that is selected may be known to affect stimulation intensity. The process of modifying the stimulation parameter value and delivering stimulation according at the respective stimulation intensity level may be repeated until a threshold physiological response is observed (e.g., based on a signal generated by an implanted or external sensor or patient input indicating a perception of a physiological event). In this way, the process of finding the threshold intensity level may be an iterative procedure.

The threshold physiological response may include a perception of the stimulation by the patient, or an observed response of a muscle that is driven by the nerve being stimulated at the target site, for example, a sphincter contraction, a toe twitch, or a detected signal on an electromyography (EMG). Other physiological responses may be detected when stimulating other nerves of the patient. In some examples, perception of the stimulation by the patient may occur prior to an observed response of a muscle that is being driven by the nerve being stimulated. In other words, the perception of the stimulation by the patient may occur at a lower threshold than the motor threshold.

In one example, the threshold intensity level may be determined by setting the stimulation frequency at about 10 Hz to about 14 Hz and increasing the current amplitude until a muscle response is observed based on a sensor input (e.g., EMG indicating the muscle movement) or patient input (e.g., perception of the stimulation by the patient).

The threshold intensity, in terms of amplitude, may define an amplitude of stimulation that produces the threshold response. The amplitude of stimulation that produces the threshold response may be referred to as a threshold amplitude. The iterative procedure described above may be used to determine the threshold amplitude. For example, amplitude of stimulation delivered to the target site may be iteratively increased until a threshold response of the patient is detected. The threshold amplitude may be roughly equal to or less than the amplitude of stimulation that produced the threshold response. Subsequent to determination of the threshold amplitude, the IMD may be programmed to select an amplitude of stimulation according to a desired response. For example, the IMD may set the amplitude of stimulation to less than or equal to the threshold amplitude (e.g., 20% of the threshold amplitude) to produce the delayed response, or the IMD may set the amplitude of stimulation to a value that is relatively greater than the threshold amplitude (e.g., less than or equal to two times the threshold) such that the selected stimulation parameters produce electrical stimulation having an intensity greater than the threshold intensity and produce the immediate response.

In some examples, based on the determined threshold stimulation intensity, the clinician may select the stimulation parameters that define the low intensity stimulation by, for example, reducing one or more stimulation parameters such that the selected stimulation parameters produce electrical stimulation having an intensity less than the threshold intensity. The clinician may reduce the intensity to any value as long as the resulting stimulation parameters are still sufficient to induce the post-stimulation, desired therapeutic effect (e.g., a reduction in bladder contraction frequency following initiation of the low intensity stimulation). Similarly, the clinician may select the stimulation parameters that define the high intensity stimulation by, for example, increasing intensity to induce an immediate therapeutic effect (e.g., a reduction in bladder contraction frequency).

The IMD may generate and deliver electrical stimulation according to a therapy cycle stored in the IMD or in another device. The therapy cycle includes a period of time in which a relatively low intensity stimulation is delivered to the patient, a transition period in which the IMD increases stimulation from the low intensity level to the high intensity level, and, in some examples, a time period in which the high intensity stimulation is delivered to the patient. Each therapy cycle may be defined by one or more therapy programs, which each define values for a set of therapy parameters (also referred to as stimulation parameters). For example, each therapy cycle may be defined by at least one therapy program that defines the low intensity stimulation, a first duration of time during which the low intensity stimulation is delivered to the patient, at least one therapy program that defines the high intensity stimulation, and a transition period during which stimulation intensity is increased from the low intensity level to the high intensity level. In some examples, a therapy cycle is also defined by one or more therapy programs that define stimulation delivered during the transition period.

Each therapy program defines one or more therapy parameter values. Examples of therapy parameter values include an electrode configuration, voltage or current amplitude and frequency of electrical stimulation, and, in the case of stimulation pulses, pulse width or pulse rate. Electrode configuration (also referred to as an electrode combination) may refer to both a subset of electrodes with which the IMD delivers stimulation to the patient and the polarities of the electrodes, e.g., as a cathode or anode.

In some examples, the IMD may control the intensity of stimulation and the duration for which the intensity of stimulation is applied based on the therapy cycle. For example, the IMD may deliver a low intensity electrical stimulation to a patient for a period of time, and then gradually increases the intensity of electrical stimulation from the low intensity stimulation to a relatively high intensity stimulation. The IMD may deliver the relatively low intensity electrical stimulation followed by the gradual increase in intensity to generate a physiological response in a patient that manages urgency and/or urinary incontinence. In some examples, the therapy cycle is based on a micturition cycle of the patient. For example, the IMD may increase the intensity of stimulation from a predetermined low intensity level to a predetermined high intensity level during a time period that is based on a time since the occurrence of the last voiding event of the patient. For example, the IMD may increase stimulation intensity as time passes since the last voiding event and then revert to the low intensity stimulation once a subsequent voiding event occurs.

While a relatively high intensity stimulation delivered to the patient substantially continuously may be useful for managing urgency and/or urinary incontinence (e.g., reducing or even eliminating the frequency of involuntary voiding events), the techniques described herein in which the stimulation intensity is relatively low and increases as time passes since the last voiding event may be useful for decreasing power consumption by the IMD while still maintaining the efficacy of stimulation. Additionally, the techniques described herein in which the stimulation intensity level is initially relatively low may also decreasing any adaptation of the patient to the therapy delivery while still maintaining the efficacy of stimulation. "Adaptation" may refer to a phenomenon in which a patient may adapt to stimulation delivered by an IMD over time, such that a certain level of electrical stimulation provided to a tissue site in the patient may be less effective over time.

In some examples, the IMD may provide electrical stimulation based on the therapy cycle and data received from sensors and/or patient input. In other words, the IMD may modify the electrical stimulation delivered to the patient based on sensor data and/or patient input. The intensity of stimulation may be defined by parameters such as amplitude, pulse rate, and pulse width. Accordingly, the therapy cycle may define the time course with which the IMD modifies an amplitude, pulse rate, and pulse width of a stimulation signal that is delivered to the patient and the duration for which the stimulation signal with the particular amplitude, pulse rate, and pulse width are delivered. For example, the IMD may deliver a specified intensity (e.g., amplitude, pulse rate, and pulse width) for a period of time according to a therapy cycle.

Sensor data may indicate, for example, a frequency of bladder contraction. Bladder contraction frequency may be determined based on signals received from any suitable sensor or device. For example, bladder contraction frequency may be determined using a sensor that indicates bladder impedance, bladder pressure, pudendal or sacral afferent nerve signals, external urinary sphincter electromyogram (EMG), motion (e.g., accelerometer signals), or any combination thereof.

Patient input may include data received by the IMD from a patient programmer that indicates, for example, an amount of fluid intake by the patient, an urge felt by the patient, a leakage incident experienced by the patient, an imminent voiding event predicted by the patient, an occurrence of an involuntary voiding event or an occurrence of a voluntary voiding event undertaken by the patient.

According to one example therapy cycle, the IMD may deliver low intensity stimulation immediately following a voiding event for a predetermined amount of time. For example, the IMD may deliver low intensity stimulation starting from 0-30 minutes after the voiding event, depending on the patient. Following the predetermined amount of time, the IMD may gradually increase the level of intensity from the low intensity to a high intensity. The IMD may then deliver the high intensity stimulation until a voiding event is detected, e.g., based on sensor data and/or patient input.

According to other examples, the IMD may deliver stimulation according to a therapy cycle that implements sensor data and/or patient input to modify stimulation intensity and duration in real-time. For example, the IMD may provide low intensity stimulation following a voiding event, then determine when to increase intensity from the low intensity to the high intensity based on data received from sensors and/or patient input that indicates an urge felt by the patient or an increase in bladder contraction frequency.

In still other examples, sensor data and/or patient input received during past micturition cycles may be used to modify operation of the therapy cycle for future micturition cycles. In other words, the therapy cycle that defines the intensities of stimulation applied to the patient and the durations for which the intensities are applied to the patient may be adapted to the patient based on past sensor data and/or patient input. As used herein, a "micturition cycle" may include a period of time between two voiding events.

FIG. 1 is a conceptual diagram illustrating an example therapy system 10 that delivers electrical stimulation therapy to a patient 14 to manage an urgency and/or urinary incontinence disorder of patient 14. Therapy system 10 includes an implantable medical device (IMD) 16, which is coupled to leads 18, 20, and 28, sensor 22, and external programmer 24. IMD 16 generally operates as a therapy device that delivers electrical stimulation to, for example, a tissue site proximate a pelvic floor nerve, a pelvic floor muscle, the urinary sphincter, or other pelvic floor targets. Pelvic floor nerves include peripheral nerves such as sacral nerves, pudendal nerves and associated branches, and dorsal genital nerves. In some examples, IMD 16 delivers the electrical stimulation therapy to a sacral nerve of patient 14 to generate an afferent response that relaxes bladder 12, e.g., to reduce a frequency of bladder contractions.

IMD 16 provides electrical stimulation therapy to patient 14 by generating and delivering electrical stimulation signals to a target therapy site by lead 28 and, more particularly, via electrodes 29A-29D (collectively referred to as "electrodes 29") disposed proximate to a distal end of lead 28. For example, IMD 16 may deliver low intensity stimulation therapy (e.g., subthreshold stimulation) and high intensity electrical stimulation therapy (e.g., greater than the threshold intensity) to patient 14 to elicit delayed and immediate physiological responses, respectively. IMD 16 may also deliver stimulation at intensities between the low intensity and high intensity stimulation. For example, IMD 16 may gradually transition delivery of stimulation from the low intensity to the high intensity in increments defined by, for example, a ramp function, a step function, or a curvilinear function. In some examples, IMD 16 may modify stimulation therapy intensity and duration based on sensor data and/or patient input. As one example, IMD 16 may detect an increased rate of bladder contraction based on sensor data and then modify stimulation (e.g., increase intensity) based on the detected increase in bladder contraction frequency. As another example, patient 14 may use external programmer 24 to provide patient input to IMD 16 indicating urge or an increased probability of unintentional voiding. IMD 16 may then modify stimulation based on the patient input. Modification of electrical stimulation therapy based on sensor data and/or patient input is described hereinafter in further detail.

IMD 16 may be surgically implanted in patient 14 at any suitable location within patient 14, such as near the pelvis. In some examples, the implantation site may be a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via a respective lead extension. Electrical conductors disposed within the lead bodies of leads 18, 20, and 28 electrically connect sense electrodes (not shown) and stimulation electrodes, such as electrodes 29, to a therapy delivery module (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may decrease as the volume of urine within bladder 12 increases.

One or more medical leads, e.g., leads 18, 20, and 28, may be connected to IMD 16 and surgically or percutaneously tunneled to place one or more electrodes carried by a distal end of the respective lead at a desired pelvic nerve or muscle site, e.g., one of the previously listed target therapy sites such as a sacral or pudendal nerve. In FIG. 1, leads 18 and 20 are placed proximate to an exterior surface of the wall of bladder 12 at first and second locations, respectively. Electrodes 29 of the common lead 28 may deliver stimulation to the same or different nerves. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 21, 29 of leads 18, 20, 28, respectively, may be ring electrodes, segmented electrodes or partial ring electrodes. Segmented and partial ring electrodes each extend along an arc less than 360 degrees (e.g., 90-120 degrees) around the outer perimeter of the respective lead 18, 20, 28. In examples, one or more of leads 18, 20, 28 may be, at least in part, paddle-shaped (i.e., a "paddle" lead).

In some examples, one or more of electrodes 19, 21, 29 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 14 that results from the delivery of stimulation therapy.

The illustrated numbers and configurations of leads 18, 20, and 28 and electrodes carried by leads 18, 20, and 28 are merely exemplary. Other configurations, i.e., number and position of leads and electrodes are possible. For example, IMD 16 may be coupled to additional leads or lead segments having one or more electrodes positioned at different locations in the pelvic region of patient 14. The additional leads may be used for delivering stimulation therapies to respective stimulation sites within patient 14 or for monitoring one or more physiological parameters of patient 14. In an example in which the target therapy sites for the stimulation therapies are different, IMD 16 may be coupled to two or more leads, e.g., for bilateral or multi-lateral stimulation. As another example, IMD 16 may be coupled to a fewer number of leads, e.g., just lead 28.

In some examples, IMD 16 may deliver the stimulation therapy based on patient input. In some examples, patient 14 may provide patient input using external programmer 24 or by tapping over IMD 16 when IMD 16 includes a motion sensor that is responsive to tapping. Using programmer 24, patient 14 may provide input to IMD 16 that indicates an urge felt by the patient, a leakage incident experienced by the patient, an imminent voiding event predicted by the patient, or a voluntary voiding event to be undertaken by the patient. In this way, therapy system 10 provides patient 14 with direct control of stimulation therapy.

In the illustrated example of FIG. 1, IMD 16 determines an impedance through bladder 12, which varies as a function of the contraction of bladder 12, via electrodes 19 and 21 on leads 18 and 20, respectively. In the example shown in FIG. 1, IMD 16 determines bladder impedance using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine bladder impedance based on the measurement of the transmitted electrical signal.

In the example four-wire arrangement shown in FIG. 1, electrodes 19A and 21A and electrodes 19B and 21B, may be located substantially opposite each other relative to the center of bladder 12. For example electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 18 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced and the determined voltage.

In the example of FIG. 1, IMD 16 also includes a sensor 22 for detecting changes in the contraction of bladder 12. Sensor 22 may be, for example, a pressure sensor for detecting changes in bladder pressure, electrodes for sensing pudendal or sacral afferent nerve signals, or electrodes for sensing urinary sphincter EMG signals, or any combination thereof. In examples in which sensor 22 is a pressure sensor, the pressure sensor may be a remote sensor that wireless transmits signals to IMD 16 or may be carried on one of leads 18, 20, or 28 or an additional lead coupled to IMD 16. In examples in which sensor 22 includes one or more electrodes for sensing afferent nerve signals, the sense electrodes may be carried on one of leads 18, 20, or 28 or an additional lead coupled to IMD 16. In examples in which sensor 22 includes one or more sense electrodes for generating a urinary sphincter EMG, the sense electrodes may be carried on one of leads 18, 20, or 28 or additional leads coupled to IMD 16. In any case, in some examples, IMD 16 may control the intensity and duration of electrical stimulation based on input received from sensor 22. For example, IMD 16 may increase the intensity of electrical stimulation when the sensor 22 indicates an increase in urge or probability of an involuntary voiding event of patient 14, such as when an increase in bladder pressure is detected by sensor 22.

In other examples, sensor 22 may comprise a patient motion sensor that generates a signal indicative of patient activity level or posture state. In some examples, IMD 16 controls the delivery of stimulation therapy to patient 14 based on sensed patient activity level or posture state. For example, a patient activity level that is greater than or equal to a threshold may indicate that there is an increase in urgency and/or an increase in the probability that an incontinence event will occur, and accordingly, IMD 16 may provide electrical stimulation based on the patient activity level. In one example, the IMD 16 may increase intensity of stimulation in response to a patient activity level that is greater than the threshold, since there may be an increase in urgency and/or an increase in the probability that an incontinence event may occur. The increase in intensity level may reduce the increase in urgency and/or the probability that an incontinence event may occur.

As an additional example, patient 14 may be more prone to urgency or an incontinence event when patient 14 is in an upright posture state compared to a lying down posture state. Accordingly, in some examples, IMD 16 may control the delivery of electrical stimulation to patient based on the patient posture state determined based on a signal generated by sensor 22. For example, IMD 16 may increase intensity of stimulation when sensor 22 indicates that patient 14 is in a posture that is more prone to urgency and/or an incontinence event in order reduce urgency and/or an increase in probability of an incontinence event.

As another example, sensor 22 may generate a signal indicative of patient motion and IMD 16 or programmer 24 may determine whether patient 14 voluntarily voided based on a pattern in the patient motion signal associated with a voluntary voiding event alone or in combination with other sensed parameters (e.g., bladder impedance).

System 10 includes an external programmer 24, as shown in FIG. 1. In some examples, programmer 24 may be a wearable communication device, handheld computing device, computer workstation, or networked computing device. Programmer 24 may include a user interface that receives input from a user (e.g., patient 14, a patient caretaker or a clinician). The user interface may include a keypad and a display (e.g., an LCD display). The keypad may take the form of an alphanumeric keypad or a reduced set of keys associated with particular functions of programmer 24. Programmer 24 can additionally or alternatively include a peripheral pointing device, such as a mouse, via which a user may interact with the user interface. In some examples, a display of programmer 24 may include a touch screen display, and a user may interact with programmer 24 via the touch screen display. It should be noted that the user may also interact with programmer 24 and/or IMD 16 remotely via a networked computing device.

Patient 14 may interact with programmer 24 to control IMD 16 to deliver the stimulation therapy, to manually abort the delivery of the stimulation therapy by IMD 16 while IMD 16 is delivering the therapy or is about to deliver the therapy, or to inhibit the delivery of the stimulation therapy by IMD 16, e.g., during voluntary voiding events. Patient 14 may, for example, use a keypad or touch screen of programmer 24 to cause IMD 16 to deliver the stimulation therapy, such as when patient 14 senses that a leaking episode may be imminent. In this way, patient 14 may use programmer 24 to control the delivery of the stimulation therapy "on demand," e.g., when extra stimulation therapy is desirable.

Patient 14 may interact with programmer 24 to inhibit the delivery of the stimulation therapy during voluntary voiding events or to modify the type of stimulation therapy that is delivered (e.g., to control IMD 16 to deliver stimulation therapy to help patient 14 voluntarily void in examples in which patient 14 has a urinary retention disorder). That is, patient 14 may use programmer 24 to enter input that indicates the patient will be voiding voluntarily. When IMD 16 receives the input from programmer 24, IMD 16 may suspend delivery the stimulation therapy for a predetermined period of time, e.g., two minutes, to allow the patient to voluntarily void, or switch to a different type of stimulation therapy to help patient 14 voluntarily void.

A user, such as a physician, technician, surgeon, electrophysiologist, or other clinician, may also interact with programmer 24 or another separate programmer (not shown), such as a clinician programmer to communicate with IMD 16. Such a user may interact with a programmer to retrieve physiological or diagnostic information from IMD 16. The user may also interact with a programmer to program IMD 16, e.g., select values for the stimulation parameter values of the therapy cycle with which IMD 16 generates and delivers electrical stimulation and/or the other operational parameters of IMD 16. For example, the user may use programmer 24 to retrieve information from IMD 16 regarding the contraction of bladder 12 and voiding events. As another example, the user may use programmer 24 to retrieve information from IMD 16 regarding the performance or integrity of IMD 16 or other components of system 10, such as leads 18, 20, and 28, or a power source of IMD 16.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In some examples, IMD 16 controls the transition from a low intensity level of stimulation to a high intensity level of stimulation based on patient input from programmer 24 and/or sensor data (e.g., generated by sensor 22). Sensor data may include measured signals relating to urgency and/or urinary incontinence, e.g., bladder impedance, bladder pressure, pudendal or sacral afferent nerve signals, a urinary sphincter EMG, or any combination thereof. As another example, sensor data may include, and IMD 16 may deliver stimulation therapy in response to, measured signals relating to a patient activity level or patient posture state. In some instances, sensor data may be indicative of an increased probability of an occurrence of an involuntary voiding event. IMD 16 may increase intensity of stimulation to prevent an involuntary voiding event in response to sensor data that indicates an increase in probability of an involuntary voiding event. On the other hand, IMD 16 may decrease intensity of stimulation when sensor data indicates a decrease in probability of an involuntary voiding event.

According to one example therapy cycle, IMD 16 may generate and deliver low intensity stimulation to the tissue site within patient 14 proximate a pelvic floor nerve following a voluntary or involuntary voiding event for a predetermined amount of time. Immediately following the predetermined amount of time and during a transition period, IMD 16 may gradually increase the level of intensity from the low intensity to a high intensity. IMD 16 delivers stimulation to patient 14 in accordance with a plurality of intermediate intensity levels between the low intensity level and the high intensity level during the transition period. IMD 16 may then deliver the high intensity stimulation until a voiding event is detected, e.g., based on sensor data and/or patient input. In this way, IMD 16 may deliver low intensity stimulation to the tissue site for a predetermined period when the patient's urge to void is likely low (e.g., immediately after a voiding event), and then subsequently increase the intensity of stimulation to the high intensity stimulation in order to address an increasing urge to void or likelihood of unintentional voiding.

Bladder contractions may be less frequent immediately after a voiding event and/or the possibility of an involuntary voiding event may be relatively low immediately after a voiding event. Therefore, the low intensity stimulation may be effective in preventing or at least minimizing the possibility of an involuntary voiding event during the time period immediately following the occurrence of a voluntary or involuntary voiding event. In contrast, bladder contractions may be more frequent as time passes since the last voiding event and/or the possibility of an involuntary voiding event may increase as time passes since the last voiding event. Increasing an intensity of stimulation as the time passes since a most recent voiding event (e.g., the last voiding event) and prior to a subsequent voiding event may help adapt the stimulation therapy to address an increasing urge to void or likelihood of unintentional voiding that may result following the voiding event. The relatively high intensity stimulation may be used as a way to immediately prevent urge and unintentional voiding just prior to an intentional voiding event.

According to other examples, IMD 16 may provide stimulation based on a therapy cycle that implements sensor data and/or patient input. For example, IMD 16 may generate and deliver a low intensity stimulation immediately following a voiding event (e.g., prior to any delivery of a higher intensity stimulation relative to the voiding event), and then determine when to increase intensity from the low intensity to the high intensity based on sensor data and/or patient input. Sensor data and/or patient input may indicate, for example, an increase in urge to void or an increase in probability that an involuntary voiding event may occur. Accordingly, IMD 16 may, in response to sensor data and/or patient input that indicates an increase in urge to void or an increase in the probability of an involuntary voiding event, increase intensity of electrical stimulation in order to immediately control the increase in urge or possible unintentional voiding.

In still other examples, sensor data and/or patient input received during past micturition cycles may be used to modify the therapy cycle (e.g., a duration of the time period in which the low intensity stimulation is delivered to patient 14, to modify a duration of the transition period, or to modify the intensity levels of the transition period) for future micturition cycles. In other words, IMD 16 may adapt the therapy cycle to patient 14 based on sensor data and/or patient input received in the past.

In some examples, the therapy cycle may be defined based on a training period during which sensor data and/or patient input is received and response of the patient to electrical stimulation is characterized. In some cases, the training period may take place prior to chronic therapy delivery by IMD 16. Various parameters relating to the micturition cycle of patient 14 may also be determined during the training period, during which historic micturition cycle data is obtained. Examples parameters include, for example, the mean, median, shortest or longest duration of a voiding event, the mean, median, shortest or longest duration between voiding events, and the like. Based on at least one of the sensor data, patient input, response of patient 14 to electrical stimulation during the training period, and/or the historical micturition cycle information, a therapy cycle that is adapted to patient 14 may be defined. In some implementations, the adapted therapy cycle may operate in an open loop fashion, e.g., without sensor data and patient input. In other implementations, the adapted therapy cycle may operate based on patient input and/or sensor data. In implementations in which the adapted therapy cycle operates based on feedback, the adapted therapy cycle may be continuously adapted to patient 14 from one micturition cycle to the next. In other words, electrical stimulation applied during a micturition cycle may be based not only on sensor data and/or patient input received during that micturition cycle, but may also be based on sensor data and/or patient input received during one or more prior micturition cycles.

Figure 2:
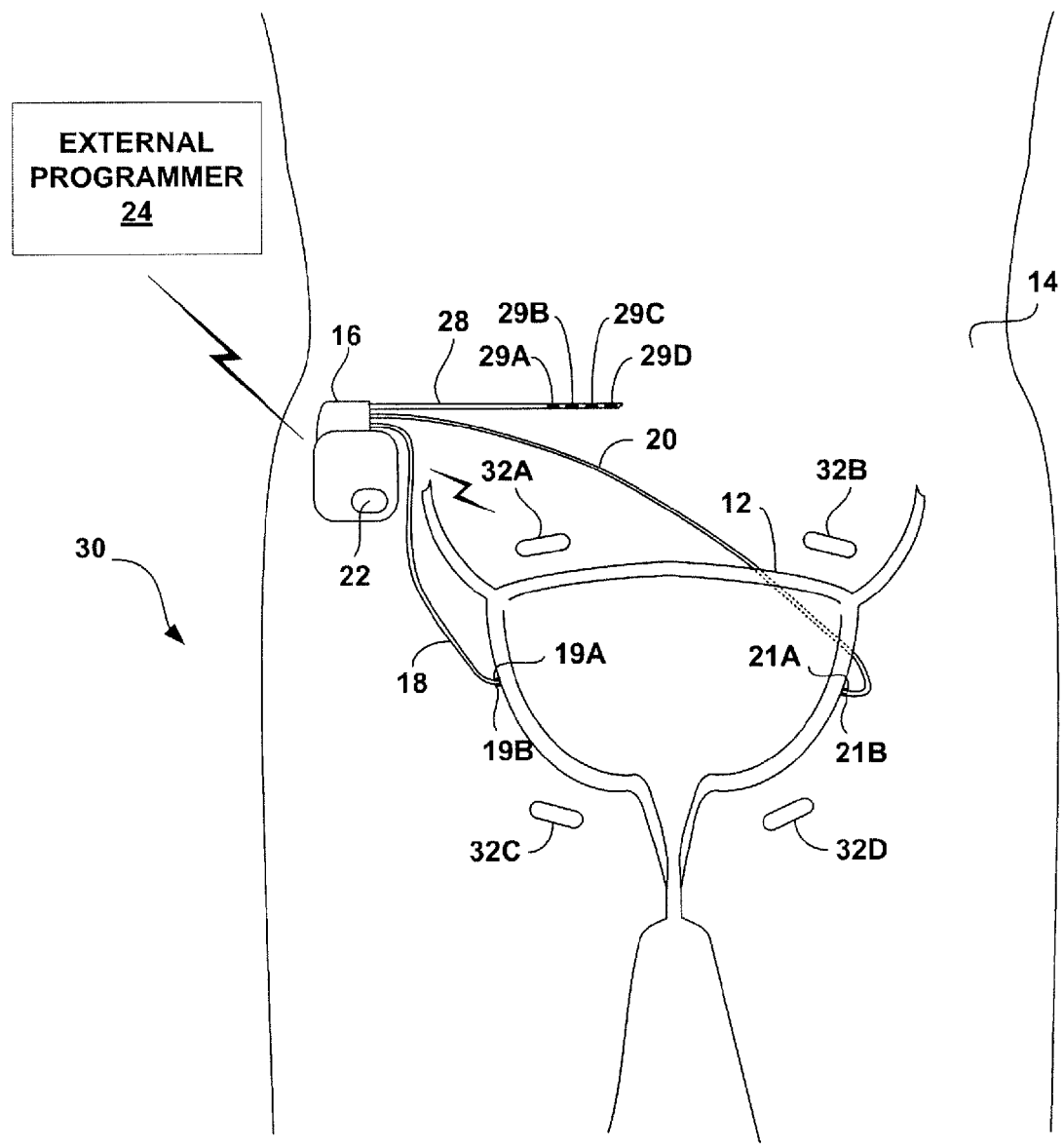
FIG. 2 is a conceptual diagram illustrating another example therapy system that delivers stimulation therapy to a patient to manage urgency and urinary incontinence.

FIG. 2 is conceptual diagram illustrating another example therapy system 30 that delivers stimulation therapy to manage an urgency and/or urinary incontinence condition of patient 14. Therapy system 30 includes a distributed array of electrical stimulators, referred to herein as microstimulators 32A-32D (collectively referred to as "microstimulators 32"), in addition to IMD 16, leads 18, 20, and 28, sensor 22, and programmer 24. Microstimulators 32 are configured to generate and deliver electrical stimulation therapy to patient 14 via one or more electrodes. Microstimulators 32 have a smaller size than IMD 16, and are typically leadless.

IMD 16 may deliver electrical stimulation therapies to patient 14 via microstimulators 32. For example, IMD 16 may communicate wirelessly with microstimulators 32 via wireless telemetry to control delivery of the stimulation therapies via microstimulators 32. In the example of FIG. 2, microstimulators 32 are implanted at different target stimulation sites. For example, microstimulators 32A and 32B may be positioned to stimulate a different set of nerves than microstimulators 32C and 324D. As an example, microstimulators 32A and 32B may target sacral nerves, while microstimulators 32C and 32D target the pudendal nerve. In other examples, microstimulators 32 may be implanted at various locations within the pelvic floor region, e.g., at different positions in proximity to the sacrum to target different nerves within the pelvic region. The illustrated number and configuration of microstimulators 32 is merely exemplary. Other configurations, i.e., number and position of microstimulators, are possible.

Systems 10 and 30 shown in FIGS. 1 and 2, respectively, are merely examples of therapy systems that may provide a stimulation therapy to manage urgency and/or urinary incontinence. Systems with other configurations of leads, electrodes, and sensors are possible. Additionally, in other examples, a system may include more than one IMD.

Figure 3:
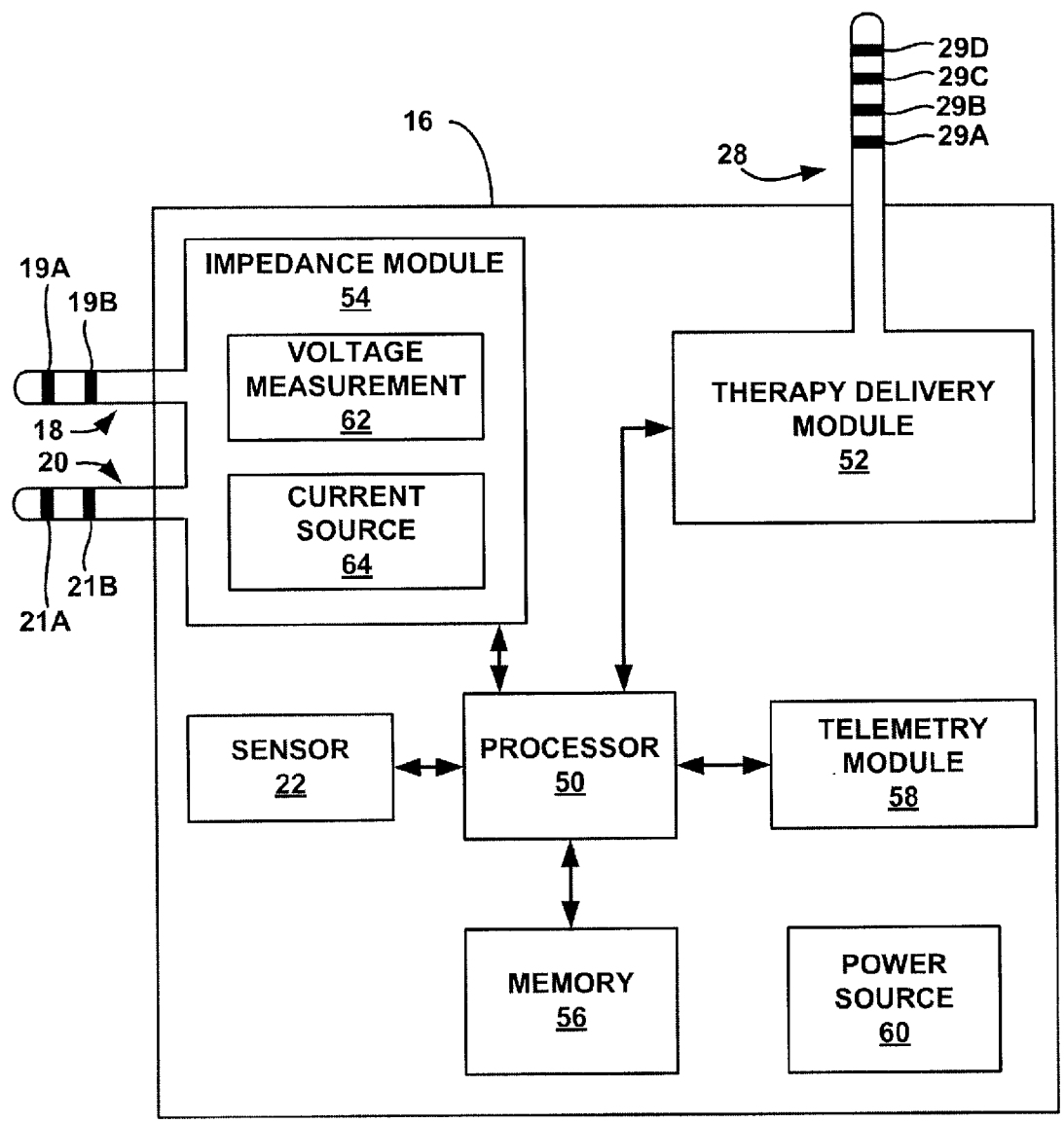
FIG. 3 is a functional block diagram illustrating an example configuration of the implantable medical device (IMD) of the systems shown in FIGS. 1 and 2.

FIG. 3 is a functional block diagram illustrating example components of IMD 16. In the example of FIG. 3, IMD 16 includes sensor 22, processor 50, therapy delivery module 52, impedance module 54, memory 56, telemetry module 58, and power source 60.

Memory 56 stores therapy cycles that specify intensities of stimulation and durations for which the intensities are applied. Therapy delivery module 52 generates and delivers electrical stimulation under the control of processor 50. In particular, processor 50 controls therapy delivery module 52 by accessing memory 56 to selectively access and load therapy programs of a therapy cycle into therapy delivery module 52. Therapy delivery module 52 generates and delivers electrical stimulation according to the therapy cycles. For example, therapy delivery module 52 may generate and deliver electrical stimulation based on the intensities and durations specified by the therapy cycles. In some examples, therapy delivery module 52 generates therapy in the form of electrical pulses. In other examples, therapy delivery module 52 may generate electrical stimulation in the form of continuous waveforms.

Patient 14 may provide patient input to IMD 16 using programmer 24 or another device, or directly via IMD 16. For example, patient 14 may provide patient input to IMD 16 using sensor 22 when sensor 22 includes a motion sensor that is responsive to tapping (e.g., by patient 14) on skin superior to IMD 16. When sensor 22 includes a motion sensor that is responsive to tapping, upon detecting the pattern of tapping that indicates a particular patient input, processor 50 may determine that the patient input was received.

Regardless of whether patient input is received from programmer 24 or other device, the patient input may indicate an urge felt by patient 14, a leakage incident experienced by patient 14, an imminent voiding event predicted by patient 14, a voluntary voiding event undertaken by patient 14 or other information that may affect the timing or intensity level of stimulation delivered by IMD 16.

In some examples, processor 50 receives the patient input from programmer 24 via telemetry module 58 and controls therapy delivery module 52 to deliver therapy based on the patient input. For example, if the patient input indicates the occurrence of an involuntary or voluntary voiding event, therapy delivery module 52, under the control of processor 50, may restart a therapy cycle upon receiving the patient input, such that therapy delivery module 52 generates and delivers therapy to patient 14 at the low intensity level during a time period immediately following the occurrence of the voiding event. As another example, if the patient input indicates an imminent involuntary voiding event may occur or indicates patient 14 sensed an urge, therapy delivery module 52, under the control of processor 50, may decrease the transition period from low intensity to high intensity such that the higher intensity stimulation is delivered to patient 14 in a responsive manner to help abate the occurrence of the involuntary voiding event.

A clinician or patient 14 may select a particular therapy cycle from a list of therapy cycles displayed on programmer 24, then therapy deliver module 52, under control of processor 50, may deliver stimulation therapy based on the particular therapy cycle selected by patient 14. Accordingly, in some examples, patient input may include a selected therapy cycle.

In the example of FIG. 3, therapy delivery module 52 is electrically coupled to a single lead 28, and therapy delivery module 52 delivers electrical stimulation to a tissue site of patient 14 via selected electrodes 29A-29D carried by lead 28. A proximal end of lead 28 extends from the housing of IMD 16 and a distal end of lead 28 extends to one or more target therapy sites within the pelvic floor, such as tissue sites proximate a sacral nerve, a pudendal nerve, a hypogastric nerve, a urinary sphincter, or any combination thereof. In other examples, therapy delivery module 52 may deliver electrical stimulation with electrodes on more than one lead and each of the leads may carry one or more electrodes. The leads may be configured as axial leads with ring electrodes and/or paddle leads with electrode pads arranged in a two-dimensional array. Additionally, or alternatively, the leads may include segmented and/or partial ring electrodes. The electrodes may operate in a bipolar or multi-polar configuration with other electrodes, or may operate in a unipolar configuration referenced to an electrode carried by the device housing or "can" of IMD 16. In yet other examples, such as system 30 shown in FIG. 2 that includes microstimulators 32, processor 50 may act as a "master" module that controls microstimulators to deliver stimulation at target therapy sites. In other examples, however, one of microstimulators 32 may act as a master module or microstimulators 32 may be self-controlled.

In some examples, processor 50 controls therapy module 52 to deliver the stimulation therapy to patient 14 based on signals received from impedance module 54, sensor 22, or patient input received via telemetry module 58. In the example shown in FIG. 3, processor 50 monitors bladder impedance to detect bladder contractions based on signals received from impedance module 54. For example, processor 50 may determine an impedance value based on signals received from impedance module 54, and a particular impedance value may be associated with a bladder contraction frequency (e.g., based on data obtained during a programming period). Therapy module 52 may deliver electrical stimulation therapy to patient 14 based on detection of bladder contraction using impedance module 54. For example, therapy module 52 may increase intensity of electrical stimulation in response to detection of an impedance value that indicates that bladder contraction frequency is increasing in order to address a possible increase in urge to void or likelihood of unintentional voiding. In other examples, therapy module 52 may increase intensity of electrical stimulation in response to detection of an impedance value (e.g., a low impedance value) that indicates that the bladder is filling in order to address a possible increase in urge to void or likelihood of unintentional voiding. In still other examples, therapy module 52 may decrease the intensity of stimulation (e.g., to the low intensity level) based on detection of an impedance value (e.g., a high impedance value) that indicates that the bladder is empty, for example, after a voiding event.

In the example of FIG. 3, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, processor 50 may periodically control current source 64 to, for example, source an electrical current signal through electrode 19A and sink the electrical current signal through electrode 21A. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Processor 50 determines an impedance value from the measured voltage values received from voltage measurement circuitry 52.

Processor 50 may detect a patient condition indicative of urgency and/or a high probability of an incontinence event (e.g., a relatively high bladder contraction frequency or abnormal detrusor muscle activity) based on signals received from sensor 22 in addition to, or instead of, impedance module 54. In examples in which sensor 22 includes a pressure sensor, processor 50 may determine a bladder pressure value based on signals received from the pressure sensor. Processor 50 may determine whether contractions of bladder 12 are indicative of urgency and/or an imminent incontinence event, for example, based on comparison of the sensed pressure to a pressure threshold that indicates an imminent event. For example, processor 50 may detect urgency and/or an imminent incontinence event when the sensed pressure is greater than the pressure threshold. Accordingly, in some examples, therapy delivery module 52, under control of processor 50, may increase intensity of stimulation when sensed pressure is greater than the pressure threshold.

In examples in which sensor 22 includes an EMG sensor, processor 50 may generate an EMG from the received signals generated by sensor 22 (e.g., which may sense the muscle activity with one or more sensors positioned near a target muscle) and compare the EMG to templates stored in memory 56 to determine whether the contractions of bladder 12 are indicative of urgency and/or an imminent incontinence event. For example, therapy delivery module 52 may, under control of processor 50, increase intensity of stimulation when the comparison of the EMG to the templates indicates an imminent event.

In examples in which sensor 22 includes a motion sensor, processor 50 may determine a patient activity level or posture state based on a signal generated by sensor 22. For example, processor 50 may determine a patient activity level by sampling the signal from sensor 22 and determining a number of activity counts during a sample period, where a plurality of activity levels are associated with respective activity counts. In one example, processor 50 compares the signal generated by sensor 22 to one or more amplitude thresholds stored within memory 56, and identifies each threshold crossing as an activity count.

Processor 50 may determine a patient posture state based on a signal from sensor 22 using any suitable technique. In one example, a posture state may be defined as a three-dimensional space (e.g., a posture cone or toroid), and whenever a posture state parameter value, e.g., a vector from a three-axis accelerometer of sensor 22 resides within a predefined space, processor 50 indicates that patient 14 is in the posture state associated with the predefined space.

Certain posture states or activity levels may be associated with a higher incidence of urgency and/or incontinence events. For example, patient 14 may have less control of the pelvic floor muscles when occupying an upright posture state or when patient 14 is in a highly active state (e.g., as indicated by a stored activity count or a threshold activity signal value). Thus, detection of these activity levels or posture states may be triggers for the delivery of the high intensity stimulation therapy. For example, therapy delivery module 52 may, under control of processor 50, increase intensity of stimulation when sensed activity levels or patient posture indicates an increase in urgency and/or an increased probability that an incontinence event may occur.

The threshold values or templates (e.g., indicating a signal indicative of an imminent event) stored in memory 56 may be determined using any suitable technique. In some examples, the threshold values may be determined during implantation of IMD 16 or during a trial period in a clinician's office following the implant procedure. For example, a clinician may record impedance values during involuntary voiding events and use the recorded impedance values or values calculated based on the recorded values as threshold values. These threshold values may be adapted over time based on patient input, e.g., via external programmer 24. As an example, patient 14 may indicate, via programmer 24, when an involuntary voiding event takes place. When the patient input is received, processor 50 may determine an impedance value during the event or immediately prior to the event based on signals received from impedance module 54. A new threshold value may be determined using this impedance value. For example, the threshold value stored may be a running average of impedance values measured during involuntary voiding events.

In some examples, IMD 16 includes impedance sensing module 54 and not sensor 22, while in other examples, IMD 16 includes sensor 22, but not impedance sensing module 54. Moreover, in some examples, sensor 22 and/or impedance sensing module 54 may be physically separate from IMD 16. Physically separate sensors may be useful in examples in which either sensor 22 and/or impedance sensing module 54 sense one or more physiological parameters at a location that is not accessible by IMD 16 or difficult to access by IMD 16.

Processor 50 may control therapy delivery module 52 to deliver stimulation therapy based on patient input received via telemetry module 58. Telemetry module 58 includes any suitable hardware, firmware, software or any combination thereof for communicating with another device, such as programmer 24 (FIG. 1). Under the control of processor 50, telemetry module 58 may receive downlink telemetry, e.g., patient input, from and send uplink telemetry to programmer 24 with the aid of an antenna, which may be internal and/or external. Processor 50 may provide the data to be uplinked to programmer 24 and the control signals for the telemetry circuit within telemetry module 58, and receive data from telemetry module 58.

Processor 50 may control telemetry module 58 to exchange information with medical device programmer 24. Processor 50 may transmit operational information and receive stimulation programs or stimulation parameter adjustments via telemetry module 58. Also, in some examples, IMD 16 may communicate with other implanted devices, such as stimulators, control devices, or sensors, via telemetry module 58.

The processors described in this disclosure, such as processor 50 and processing circuitry in impedance module 54 and other modules, may be one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. In some examples, the processing circuitry of impedance module 54 that determines an impedance based on a measured voltage and/or current of a signal may be the same microprocessor, ASIC, DSP, or other digital logic circuitry that forms at least part of processor 50.

Memory 56 stores instructions for execution by processor 50, in addition to therapy cycles. In some examples, memory 56 store patient parameter information, such as information generated by impedance module 54 and/or sensor 22. For example, information related to measured impedance and determined posture may be recorded for long-term storage and retrieval by a user, or used by processor 50 for adjustment of stimulation parameters, such as amplitude, pulse width, and pulse rate. Memory 56 may include separate memories for storing instructions, electrical signal information, programs, and other data.

Memory 56 may include any volatile, non-volatile, magnetic, or electrical media, such as a random access memory (RAM), read-only memory (ROM), non-volatile RAM (NVRAM), electrically-erasable programmable ROM (EEPROM), flash memory, and the like. Memory 56 may store program instructions that, when executed by processor 50, cause IMD 16 to perform the functions ascribed to IMD 16 herein.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever stimulation therapy is to occur.

Figure 4:
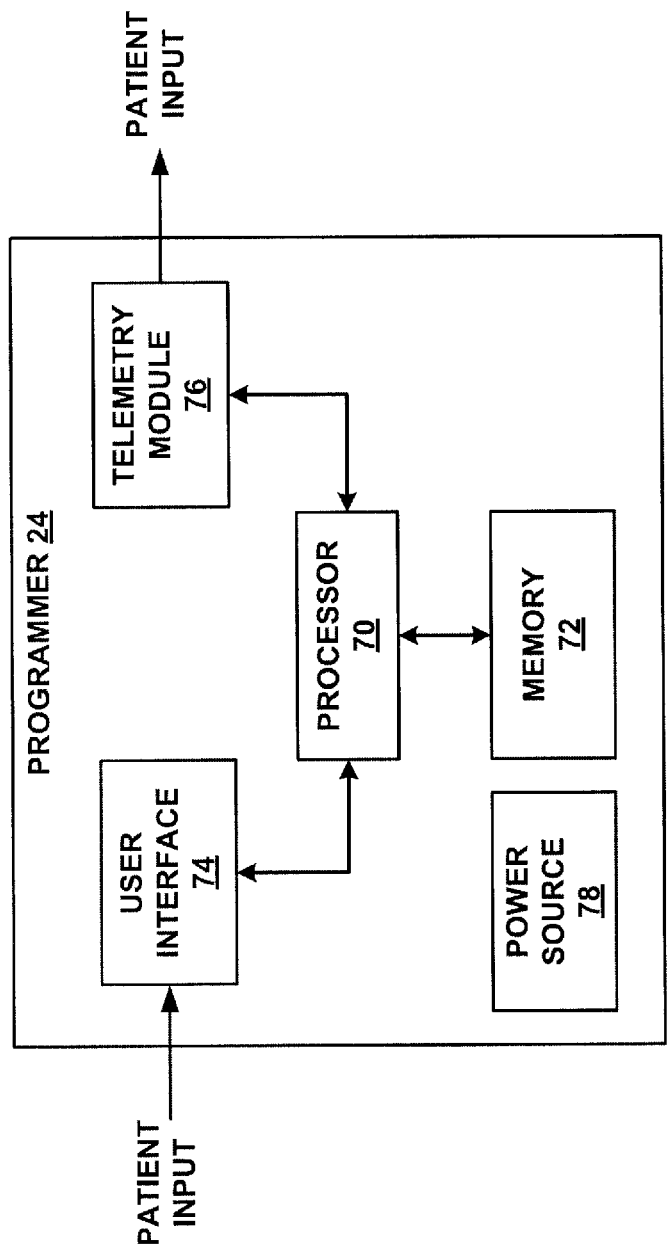
FIG. 4 is a functional block diagram illustrating an example configuration of the external programmer of the systems shown in FIGS. 1 and 2.

FIG. 4 is a functional block diagram illustrating example components of external programmer 24. While programmer 24 may generally be described as a hand-held computing device, the programmer may be a notebook computer, a cell phone, or a workstation, for example. As illustrated in FIG. 4, external programmer 24 may include a processor 70, memory 72, user interface 74, telemetry module 76, and power source 78. Memory 72 may store program instructions that, when executed by processor 70, cause processor 70 to provide the functionality ascribed to programmer 24 throughout this disclosure.

In some examples, memory 72 may further include therapy cycles defining stimulation therapy, similar to those stored in memory 56 of IMD 16. The therapy cycles stored in memory 72 may be downloaded into memory 56 of IMD 16. Memory 72 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processor 70 can take the form one or more microprocessors, DSPs, ASICs, FPGAs, programmable logic circuitry, or the like, and the functions attributed to processor 70 herein may be embodied as hardware, firmware, software or any combination thereof.

User interface 74 may include a button or keypad, lights, a speaker for voice commands, and a display, such as a liquid crystal (LCD). In some examples the display may be a touch screen. As discussed in this disclosure, processor 70 may present and receive information relating to stimulation therapy via user interface 74. For example, processor 70 may receive patient input via user interface 74. The patient input may be entered, for example, by pressing a button on a keypad or selecting an icon from a touch screen. Patient input may include, but is not limited to, input that indicates an urge felt by the patient, a leakage incident experienced by the patient, an imminent voiding event predicted by the patient, or a voluntary voiding event to be undertaken by the patient.

Telemetry module 76 supports wireless communication between IMD 16 and external programmer 24 under the control of processor 70. Telemetry module 76 may also be configured to communicate with another computing device via wireless communication techniques, or direct communication through a wired connection. Telemetry module 76 may be substantially similar to telemetry module 58 described above, providing wireless communication via an RF or proximal inductive medium. In some examples, telemetry module 76 may include an antenna, which may take on a variety of forms, such as an internal or external antenna. An external antenna that is coupled to programmer 24 may correspond to a programming head that may be placed over IMD 16.

Examples of local wireless communication techniques that may be employed to facilitate communication between programmer 24 and another computing device include RF communication according to IEEE 802.11 or Bluetooth specification sets, infrared communication, e.g., according to an IrDA standard, or other standard or proprietary telemetry protocols. In this manner, other external devices may be capable of communicating with programmer 24 without needing to establish a secure wireless connection.

In some examples, IMD 16 and/or programmer 24 may control the timing of the delivery of electrical stimulation therapy to manage urgency and/or urinary incontinence. For example, if programmer 24 controls the stimulation, programmer 24 may control the timing of the therapy cycles or the duration of the therapy cycle by transmitting controls signals to IMD 16 via telemetry module 76. Programmer 24 may also transmit the information defining the therapy cycles to IMD 16 via telemetry module 76. For example, a user (e.g., patient 14 or a clinician) may select the therapy cycles from a predetermined list of therapy cycles provided via a display of user interface 74. In other examples, the user may generate the duration of the therapy cycles by interacting with user interface 74 of programmer. Alternatively, external programmer 24 may transmit a signal to IMD 16 indicating that IMD 16 should execute locally stored programs or therapy cycles. In such a manner, control over the electrical stimulation may be distributed between IMD 16 and external programmer 24, or may reside in either one alone. In some examples, patient 14 may provide input via programmer 24 to restart a therapy cycle, e.g., upon the occurrence of a voiding event, or to increase the intensity of stimulation, such as when patient 14 senses the onset of a leakage episode.

In some cases, it may be desirable for IMD 16 to decrease the intensity of stimulation or even suspend the delivery of the stimulation configured to help prevent an involuntary voiding event of patient 14 when patient 14 needs to void. The decrease in intensity of stimulation or the suspension of the stimulation may help patient 14 void or may at least prevent the stimulation from interfering with the ability of patient 14 to voluntarily void. In some examples, patient 14 may interact with programmer 24 (or directly with IMD 16 as described above) to control IMD 16 to withhold the stimulation that is intended to help prevent the occurrence of an involuntary voiding event. Patient 14 may indicate an intent to void via user interface 74, and processor 70 may implement a blanking interval through communication of the indication to IMD 16 via telemetry module 76. For example, processor 70 may transmit a command signal to IMD 16 that indicates IMD 16 should temporarily suspend delivery of the stimulation therapy in response to command signal. In some cases, this may permit voluntary voiding by patient 14.

In other examples, IMD 16 may automatically determine when patient 14 is attempting to voluntary void, e.g., based on a voiding signature of an EMG signal indicative of bladder activity or based on bladder pressure or contraction. In such examples, IMD 16 may automatically suspend the delivery of electrical stimulation therapies to permit patient 14 to voluntary void. In some cases, suspension of stimulation by IMD 16 is not necessary to facilitate voiding, and stimulation may occur substantially simultaneously with the voluntary voiding. For example, the bladder volume will eventually increase to a level to trigger strong bladder contractions that prevails over the stimulation therapy to allow voiding.

Power source 78 delivers operating power to the components of programmer 24. Power source 78 may include a battery, for example a rechargeable battery. Recharging may be accomplished by using an alternating current (AC) outlet or through proximal inductive interaction between an external charger and an inductive charging coil within programmer 24.

Figure 5:
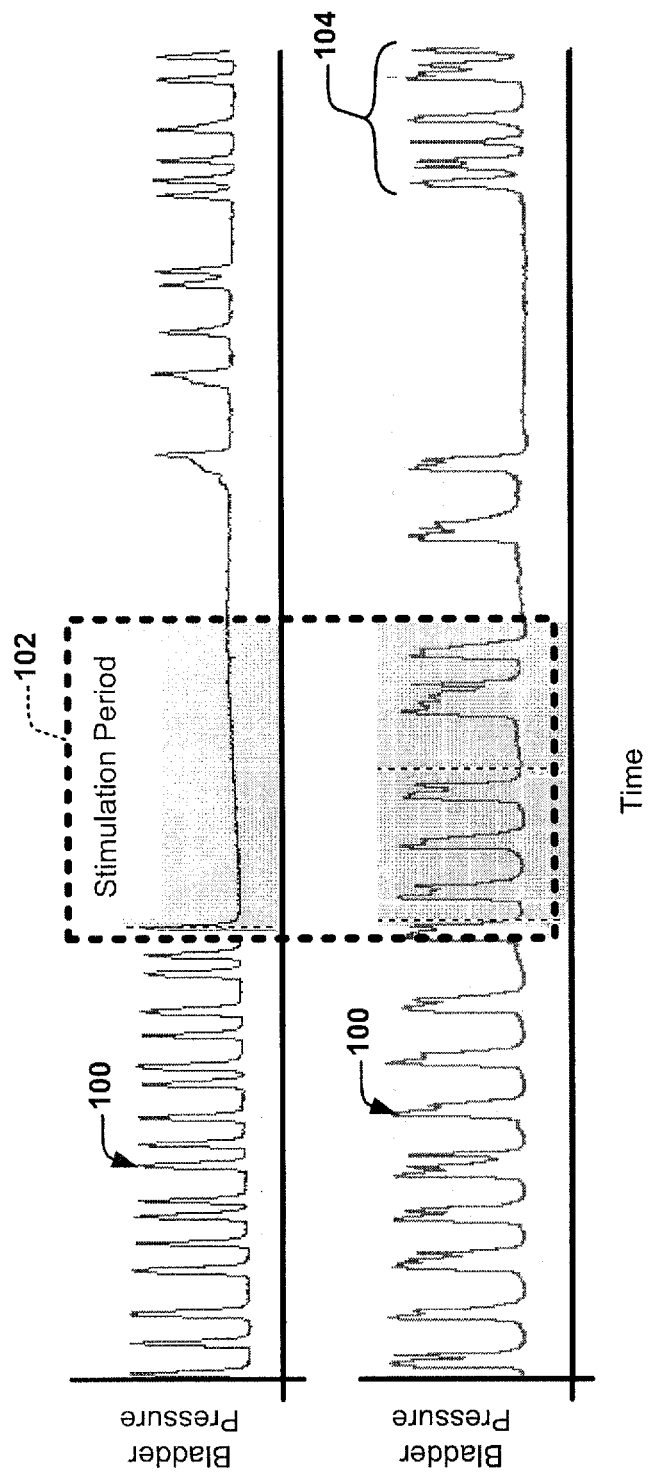
FIG. 5 is a graph that illustrates different physiological responses to low intensity stimulation and high intensity stimulation.
Figure 6:
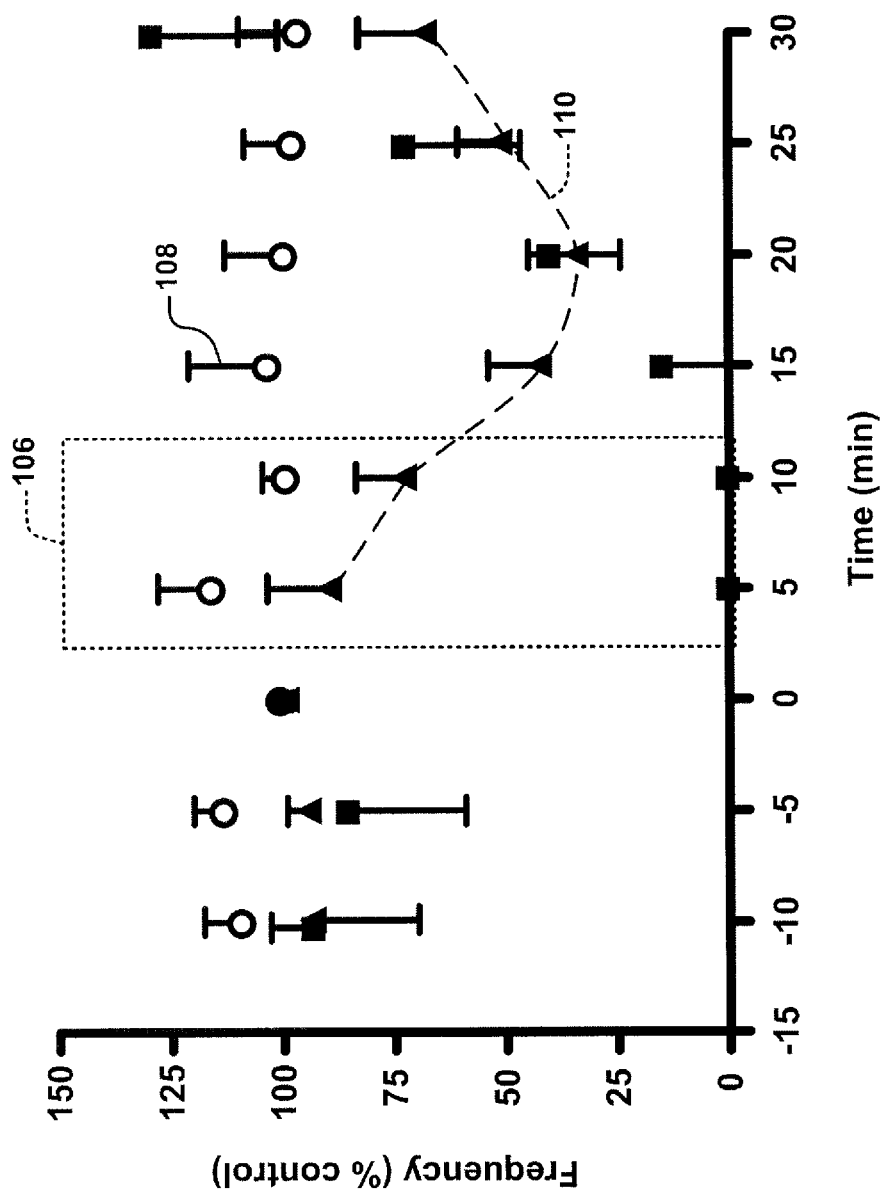
FIG. 6 is another graph that illustrates different physiological responses to low intensity stimulation and high intensity stimulation.

FIGS. 5 and 6 are graphs that include experimental data that indicates a bladder response of a rat test subject to electrical stimulation delivered to spinal nerves of the subject. It is believed that a similar physiological response to stimulation as that shown in FIGS. 5 and 6 may be applicable to human subjects. The experimental data illustrated in FIGS. 5 and 6 may indicate that, for the rat test subject, low intensity stimulation and high intensity stimulation may produce the delayed and immediate responses, respectively, described in the present disclosure.

FIG. 5 is a graph that illustrates a change in bladder contraction frequency of a rat test subject in response to spinal nerve (e.g., L6) electrical stimulation delivered to the rat test subject. In order to obtain the experimental data shown in FIG. 6, bladder contractions of one or more rat test subjects were observed while applying electrical stimulation at 10 Hz. The stimulation was delivered using biphasic pulses having pulse width of approximately 0.1 ms.

The dependent axis labeled "Frequency (% control)" indicates a frequency of bladder contractions during electrical stimulation relative to the frequency of bladder contractions before electrical stimulation was applied. In order to determine the "Frequency (% control)," bladder contraction frequencies during electrical stimulation were normalized by dividing bladder contraction frequencies during electrical stimulation by a control frequency for the rat test subject, the control frequency being the bladder contraction frequency observed prior to delivery of any electrical stimulation.

Experimental preparation and instrumentation of the rat test subjects used for collection of data in FIGS. 5-6 is now described. The rat test subjects were female Sprague-Dawley rats weighing approximately 200 grams (g) to approximately 300 g. The rat subjects were anesthetized with urethane using two intraperitoneal injections, approximately 4 minutes apart, for a total dosage of approximately 1.2 grams/kilogram. To record bladder contractions, a cannula (a PE 50—polyethylene cannula, e.g., having a 0.58 mm inner diameter) was placed into the bladder of each test subject via the urethra which was ligated to create an isovolumetric bladder. The urethral cannula was connected via a T-type connector (e.g., a three terminal connector) to a low volume pressure transducer of a data acquisition system. The other end of the T-type connector was linked to a 20 cubic centimeter (cc) syringe with a perfusion pump.

To deliver electrical stimulation, a wire electrode was placed bilaterally under the L6 spinal nerve of the test subject. The dorsal skin around the sacral and thoracic surface of the test subject was shaved and a dorsal midline incision was made from approximately spinal nerve L3 to S2. The L6/S1 posterior processes were exposed. The S1 processes were removed and the L6 nerve trunks localized caudal and medial to the sacroiliac junction. After the wire electrode was placed under each nerve with two bared portions of Teflon-coated, 40-guage, stainless steel wire, silicone adhesive was applied to cover the wire around the nerve, and sutured shut. The wire electrode was connected to a stimulus isolator (an SIU-V Grass Medical Instruments Stimulus Isolation Unit available from Astro-Med, Inc of West Warwick, R.I.) with a Grass S88 stimulator. A needle electrode under the skin of the tail of the test subject served as the ground. The stimulator generated pulses to both nerves serially.

To induce rhythmic bladder contractions, saline was infused into the bladder of the test subject at a rate of approximately 50 microliters per minute (µL/minute) to induce a micturition reflex (defined here as bladder contraction with intensity >10 millimeters of mercury (mmHg)). The infusion rate was then lowered to approximately 10 µL per minute until 3-5 consecutive contractions were established. Infusion was then terminated. After an approximately 15 minute control period, nerve stimulation was applied for about 10 minutes and the bladder rhythmic contraction (BRC) was recorded for approximately 20 minutes post stimulation. Two parameters of BRC were evaluated: frequency/interval and amplitude. Biphasic pulses (pulse width of approximately 0.1 ms) of different intensities, $T_{mot}$–6*$T_{mot}$, were used to stimulate the spinal nerve at frequencies ranging from approximately 0.01 Hz to approximately 100 Hz. $T_{mot}$ was defined as the lowest intensity to evoke the first, barely discernable muscle contraction. Any rat subject with $T_{mot}$ over 0.4 mA was excluded from the study.

The graphs of FIG. 5 illustrate bladder pressure versus time. The top graph illustrates a reduction in bladder contraction frequency in response to high intensity stimulation (e.g., at or above an intensity level that elicits the immediate physiological response). The lower graph illustrates a reduction in bladder contraction frequency in response to low intensity stimulation (e.g., at an intensity level that elicits the delayed physiological response). For example, the low intensity stimulation delivered may have corresponded to an intensity that triggered a motor threshold response of the subject. The spikes 100 may each indicate a bladder contraction. Accordingly, a number of the spikes per unit time may indicate the bladder contraction frequency. The dotted box 102 labeled "stimulation period" indicates the time period in which electrical stimulation was delivered to the spinal nerve of the rat test subject. In FIG. 5, the dotted box 102 indicates a stimulation period of approximately 10 minutes in duration.

With respect to FIG. 5, electrical stimulation was delivered to spinal nerves of the rate subject at a pulse rate of about 10 Hz and a pulse width of about 100 microseconds (µs). High intensity stimulation was delivered at an amplitude of about 0.6 mA, while low intensity stimulation was delivered at an amplitude of approximately 0.09 mA, e.g., at a motor threshold of the subject.

With respect to the upper graph of FIG. 5, bladder contraction spikes 100 are observed prior to delivery of the high intensity stimulation. The experimental data indicates that, in the test subject, the bladder contractions were reduced relative to the time period immediately preceding stimulation period 102 of high intensity stimulation. In the example of FIG. 5, bladder contraction frequency is reduced to zero immediately upon delivery of high intensity stimulation and remains zero during the delivery of the high intensity stimulation, i.e., during stimulation period 102. Bladder contraction frequency remains attenuated for a period of time after removal of the high intensity stimulation and returns approximately 20 minutes after high intensity stimulation is removed.

With respect to the lower graph of FIG. 5, bladder contraction spikes are observed prior to delivery of the low intensity stimulation. Reduction in bladder contraction frequency is not pronounced during delivery of the low intensity stimulation relative to the time period immediately preceding stimulation period 102. However, a reduction in bladder contraction frequency relative to the time period immediately preceding stimulation period 102 is pronounced after termination of the low intensity stimulation and termination of all stimulation therapy. For example, bladder contractions are reduced to zero for a period of time (e.g., 15 minutes) following removal of the low intensity stimulation. As FIG. 5 illustrates, when the low intensity stimulation was delivered to the rat subject, the physiological response was delayed such that it was observed after stimulation period 102. Bladder contractions may resume, as indicated at time period 104, subsequent to the complete reduction of bladder contractions using the low intensity stimulation.

FIG. 6 is a graph that illustrates a change in bladder contraction frequency of the rat subject in response to electrical stimulation delivered to the rat subject. The data illustrated in FIG. 6 was obtained from a plurality of tests such as the tests illustrated in FIG. 5. In order to obtain the experimental data shown in FIG. 6, bladder contractions of a plurality of rat test subjects were observed during an approximately 45 minute period (i.e., labeled from –15 min to 30 min in the graph illustrated in FIG. 6). During observation, the rat test subject was provided with electrical stimulation for a period of time, as illustrated by time period 106 shown in FIG. 6. For each test run (i.e., each 45 minute observation similar to those of FIG. 5), a frequency of bladder contractions was determined at approximately 5 minute intervals. The determined frequencies of bladder contractions were then normalized by dividing the determined frequency of bladder contractions by a control frequency for the rat test subject. The control frequency was determined to be a frequency of bladder contractions that were observed for the rat test subject prior to delivery of any stimulation, i.e., prior to stimulation period 106. The normalized bladder contraction frequencies are graphed in FIG. 6.

Regarding the units of the dependent axis. Frequency (% control) indicates a frequency of bladder contraction relative to the control frequency (i.e., the frequency before stimulation period 106). In FIG. 6, the graphed frequency (% control) ranges from approximately 0% to approximately 150%.

In the graph shown in FIG. 6, the intensity of stimulation delivered to the rat test subject is indicated by the shape of the data point. The circle data points indicate measurement of contractions in subjects that did not receive electrical stimulation. The triangle data points indicate measurement of contractions in subjects that received relatively low intensity stimulation (e.g., at a threshold intensity amplitude of approximately 0.1 mA and a pulse rate of 10 Hz). The square data points indicate measurement of contractions in subjects that received high intensity stimulation (e.g., at an amplitude of 0.6 mA and a pulse rate of 10 Hz). Each of the data points (i.e., circle, square, and triangle) includes an amount of variation. The variation bars, e.g., illustrated in one example at 108, are included to show variations among measurements amongst the plurality of rat test subjects.

The circle data points, which indicate no stimulation was delivered to the rat test subject, indicate approximately 100% bladder contraction frequency relative to the control. In other words, the circle data points are approximately equal to the control bladder contraction frequency, as expected, because electrical stimulation was not delivered to test runs indicated by the circle data points.

The square data points, which indicate the test runs in which relatively high intensity stimulation was delivered to the rat test subject, indicate a bladder contraction frequency of approximately zero during delivery of high intensity stimulation during stimulation period 106. In other words, it was observed that bladder contraction frequency was reduced to zero upon delivery of relatively high intensity stimulation to a spinal nerve of the rat test subject and remains zero during stimulation period 106 in which the high intensity stimulation was delivered to the rat test subject. It was also found that bladder contraction frequency remained attenuated for a period of time after removal of the high intensity stimulation, i.e., immediately after stimulation period 106, and gradually returned over a period of time after high intensity stimulation was removed, i.e., during a time period about 15-30 minutes immediately after stimulation period 106.

The triangle data points shown in FIG. 6 define a curve, which is illustrated by dotted line 110 in FIG. 6, which indicates a trajectory of the physiological response produced by relatively low intensity stimulation (e.g., low intensity compared to the relatively high intensity stimulation). The dip in line 110 from approximately 100% to less than 50% indicates the physiological response of the bladders of the test subjects to the low intensity stimulation. Line 110 indicates that for the test stimulation delivered to the rat test subjects, a reduction in bladder contraction frequency was observed during delivery of the low intensity stimulation during stimulation period 106, but was not significantly pronounced relative to the reduction in bladder contraction frequency observed when the high intensity stimulation was delivered. However, a reduction in bladder contraction frequency for each of the rat test subjects was pronounced after removal of the low intensity stimulation, i.e., during the time period immediately following stimulation period 106. Specifically, in the example shown in FIG. 6, bladder contractions were reduced to within about 25% to about 50% of the control frequency after stimulation period 106. This differs from the physiological response to the high intensity stimulation during the time period immediately after stimulation period 106, which immediately began to increase.

In summary, the graphs of FIGS. 5 and 6 illustrate experimentally that low intensity stimulation and high intensity stimulation may produce the delayed and immediate responses, respectively, described in the present disclosure. FIGS. 15-18C, described in further detail below, further illustrate experimental examples of the relationship between a change in intensity of electrical stimulation and a change in bladder response.

Figure 7:
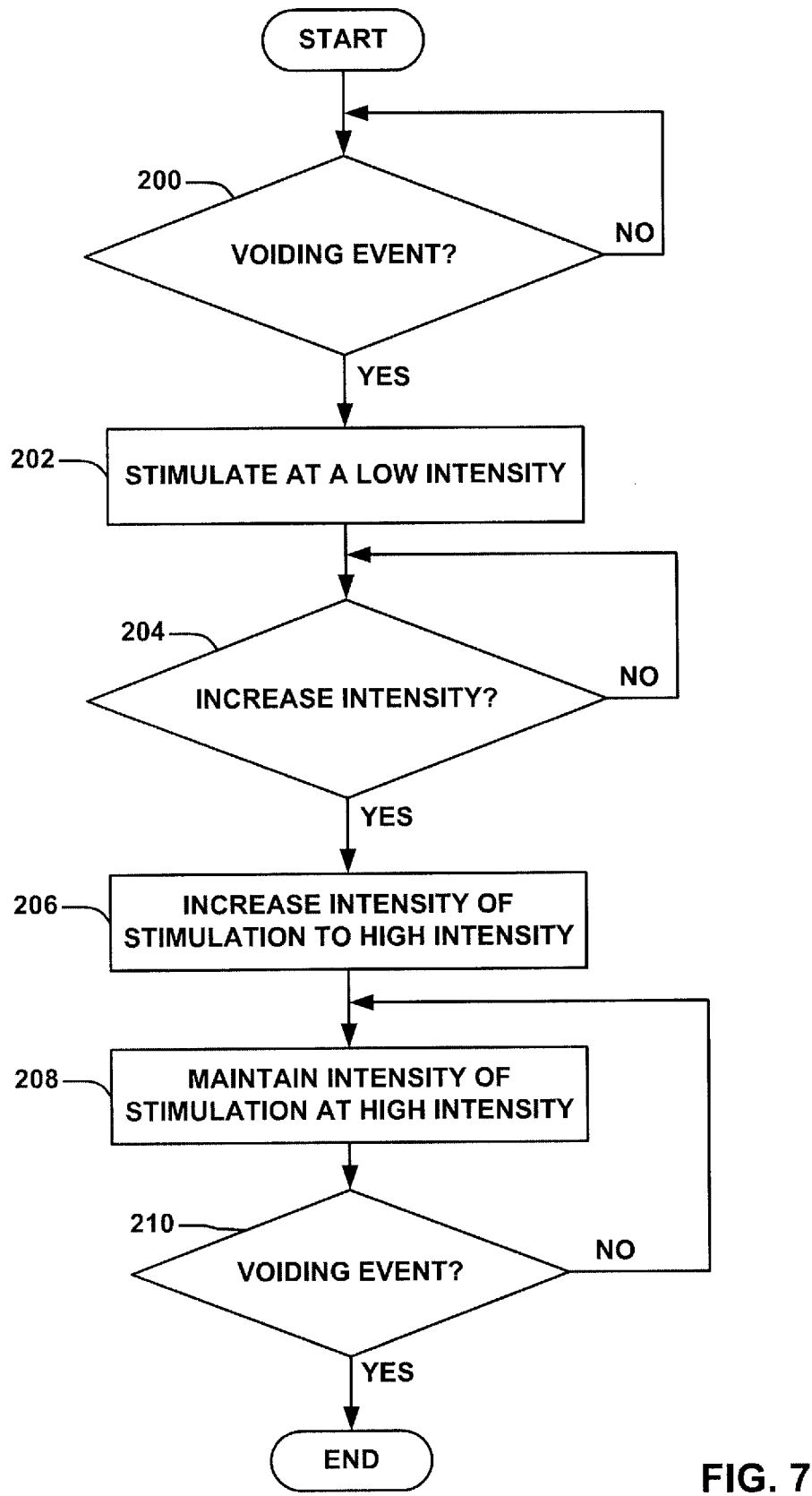
FIG. 7 is a flow diagram of an example method for delivering electrical stimulation to a patient to manage urgency and/or urge incontinence.

FIG. 7 is a flow diagram of an example method for delivering electrical stimulation to patient 14 to manage urgency and/or urinary incontinence using low intensity stimulation. In some examples, the method of FIG. 7 may be implemented as a set of instructions executable by processor 50 and stored by memory 56 of IMD 16 or a memory of another device.

While processor 50 and memory 56 are primarily referred to throughout the description of FIG. 7, in other examples, a processor of another device (e.g., programmer 24) may perform any part of the techniques described herein, including the technique shown in FIG. 7, alone or in combination with another device.

According to the example method of FIG. 7, processor 50 of IMD 16 detects a voiding event using any suitable technique (200). For example, processor 50 may detect a voiding event based on sensor data received from sensor 22 that indicates measured signals relating to bladder impedance, bladder pressure, and/or muscle activity associated with a voiding event. For example, a bladder impedance value may decrease as the volume of urine within bladder 12 increases. Accordingly, processor 50 may detect that bladder 12 has emptied based on an increase (e.g., a threshold amount of increase) in bladder impedance. As another example, processor 50 may detect that bladder 12 has emptied based on signals generated by sensor 22 that indicate a change from a bladder pressure (e.g., a threshold amount of pressure change) that indicates a relatively full bladder to a bladder pressure that indicates a relatively empty bladder. Other techniques of detecting a voiding event using a sensor may also be used. For example, in some implementations, one or more sensors that may communicate with IMD 16 or programmer 24 may be incorporated into an undergarment of patient 14 that detect wetting, fluid pH, or other characteristics that identifies fluid as urine. The sensors incorporated into the undergarment may signal processor 50 via telemetry module 58 when a voiding event occurs.

Processor 50 may also detect a voiding event based on patient input received from patient programmer 24. Patient input may include an entry of a voiding event in patient programmer 24 using user interface 74. Patient input may also include one or more taps on IMD 16 when IMD 16 includes a sensor that detects tapping.

After detection of a voiding event, processor 50 controls therapy delivery module 52 (FIG. 3) to generate and deliver electrical stimulation at a low intensity to a tissue site proximate a pelvic floor nerve of patient 14 or another suitable tissue site for controlling bladder activity of patient 14 (202). In some examples, IMD 16 delivers the low intensity electrical stimulation (202) immediately after detecting the voiding event, while in other examples, IMD 16 waits a predetermined period of time (e.g., 20 minutes) after detecting initiation of the voiding event. Delaying the delivery of the low intensity stimulation after detecting initiation of the voiding event may, for example, provide patient 14 with a window of time in which patient 14 may voluntarily void because delivering the low intensity stimulation to the tissue sites as described herein may make it more difficult to patient 14 to void.

While delivering the low intensity stimulation, processor 50 determines whether to increase stimulation intensity from the low intensity level to a higher intensity level (204). In some examples, a therapy cycle provides the time course with which processor 50 controls therapy delivery module 52 to increase the intensity of stimulation from the low intensity stimulation to the relatively high intensity stimulation. In some examples, the therapy cycle may define a predetermined period of time in which therapy delivery module 52 delivers the low intensity stimulation to patient 14. Thus, in some examples, processor 50 may increase the stimulation intensity from the low intensity after delivering the low intensity for a predetermined period of time (206).

In other examples, the therapy cycle is not predetermined, and, rather, processor 50 may control the time line with which therapy delivery module 52 increases the stimulation intensity based on sensor data and/or patient input. For example, processor 50 may control therapy delivery module 52 to begin increasing the stimulation intensity when the sensor data and/or patient input indicates one of an increased urge felt by patient 14, a leakage incident experienced by patient 14, or an imminent voiding event predicted by patient 14.

Patient 14 may indicate one of the increased urge, the leakage incident experienced, or the imminent voiding event using programmer 24, and accordingly processor 50 may detect one of the above conditions based on patient input received from patient programmer 24. Additionally, or alternatively, processor 50 may detect a bladder contraction indicative of an increased urge to void, a leakage incident experienced by patient 14, or an imminent voiding event based on bladder impedance, bladder pressure, pudendal or sacral afferent nerve signals, external urinary sphincter or anal sphincter electromyogram (EMG), motion sensor signals (e.g., accelerometer signals), or any combination thereof. For example, processor 50 may detect the increased urge to void, the leakage incident experienced by patient 14, or the imminent voiding event or other triggering event based on sensor data generated by sensor 22. For example, processor 50 may detect that bladder 12 is relatively full based on a bladder impedance value, and processor 50 may therefore indirectly detect an increased urge felt by patient 14 based on the bladder impedance value. As another example, processor 50 may detect that bladder 12 is relatively full based on signals from a bladder pressure sensor, and processor 50 may, therefore, indirectly detect an increased urge felt by patient 14 based on bladder pressure. In some implementations, one or more sensors that may communicate with IMD 16 or programmer 24 may be incorporated into an undergarment of patient 14 that detect wetting, fluid pH, or other characteristics that identifies fluid as urine. The sensors incorporated into the undergarment may signal processor 50 via telemetry module 58 when a leakage incident is experienced by patient 14. Accordingly, processor 50 may detect a leakage incident experienced by patient 14 based on data received from the sensors incorporated into the undergarment.

Upon determining the intensity of the stimulation should be increased, e.g, upon receiving the patient input or the sensor data, processor 50 may increase stimulation intensity from the low intensity to the high intensity (206). In some examples, IMD 16 abruptly increases the intensity from the low intensity level to the high intensity level (206), such as by delivering one pulse (or waveform) of the low intensity stimulation followed by a pulse (or waveform) of the high intensity stimulation. In other examples, processor 50 may control therapy delivery module 52 to gradually increase intensity from the low intensity level to the high intensity level (206), such that stimulation is delivered at a plurality of intermediate stimulation intensity levels prior to any stimulation delivered at the relatively high stimulation intensity level during the particular therapy cycle (e.g., which may begin upon the detecting of the voiding event). For example, processor 50 may control therapy delivery module 52 to gradually increase the intensity from the low intensity level to the high intensity level using a ramping or a stepping function. Regardless of how the stimulation intensity is increased, IMD 16 maintains high intensity stimulation (208) until a voiding event is detected (210). In some examples, after detection of the voiding event at block (210), IMD 16 may restart the method of FIG. 7 at bock (202).

Referring now to FIG. 8, an example configuration of IMD 16 is shown. In FIG. 8, memory 56 includes low intensity stimulation parameters 220, transition stimulation parameters 222, and high intensity stimulation parameters 224. IMD 16 may control low intensity stimulation, high intensity stimulation, and the transition from low intensity to high intensity based on the low intensity stimulation parameters 220, high intensity stimulation parameters 224, and transition stimulation parameters 222, respectively. Low intensity stimulation parameters 220, transition stimulation parameters 222, and high intensity stimulation parameters 224 may collectively define the stimulation therapy that is delivered to patient 14 during a therapy cycle. As discussed in further detail below, the therapy cycle may be restarted each time a voiding event of patient 14 is detected or based on a predetermined schedule. In some examples, at least one parameter (e.g., a low intensity therapy program, transition therapy programs, a high intensity therapy program, or the durations for delivery of therapy according to each of the therapy programs) of the therapy cycle may be modified relative to an immediately preceding therapy cycle.

In one example, low intensity stimulation parameters 220 include one or more therapy programs that define the predetermined low intensity stimulation level and the predetermined durations for which IMD 16 delivers stimulation to patient 14 at the predetermined low intensity level during a therapy program. High intensity stimulation parameters 224 include one or more therapy programs that define the high intensity stimulation level and the predetermined durations for which IMD 16 delivers stimulation to patient 14 at the high intensity level during a therapy program. Transition stimulation parameters 222 include one or more therapy programs that define the stimulation signals for the intermediate intensity levels delivered during of the transition period and the predetermined durations for which IMD 16 delivers stimulation to patient 14 at the intermediate stimulation intensity levels. For example, transition stimulation parameters 222 may define a ramping intensity or a stepping function with which processor 50 increases the stimulation intensity from the low intensity level to the high intensity level.

In further examples, to be described herein, IMD 16 may deliver electrical stimulation based on sensor data and/or patient input in addition to the low intensity stimulation parameters 220, high intensity stimulation parameters 224, and transition stimulation parameters 222. In still other examples to be described herein, IMD 16 may modify low intensity stimulation parameters 220, high intensity stimulation parameters 224, and transition stimulation parameters 222 based on at least one of sensor data and/or patient input received during past micturition cycles.

Figure 9A:
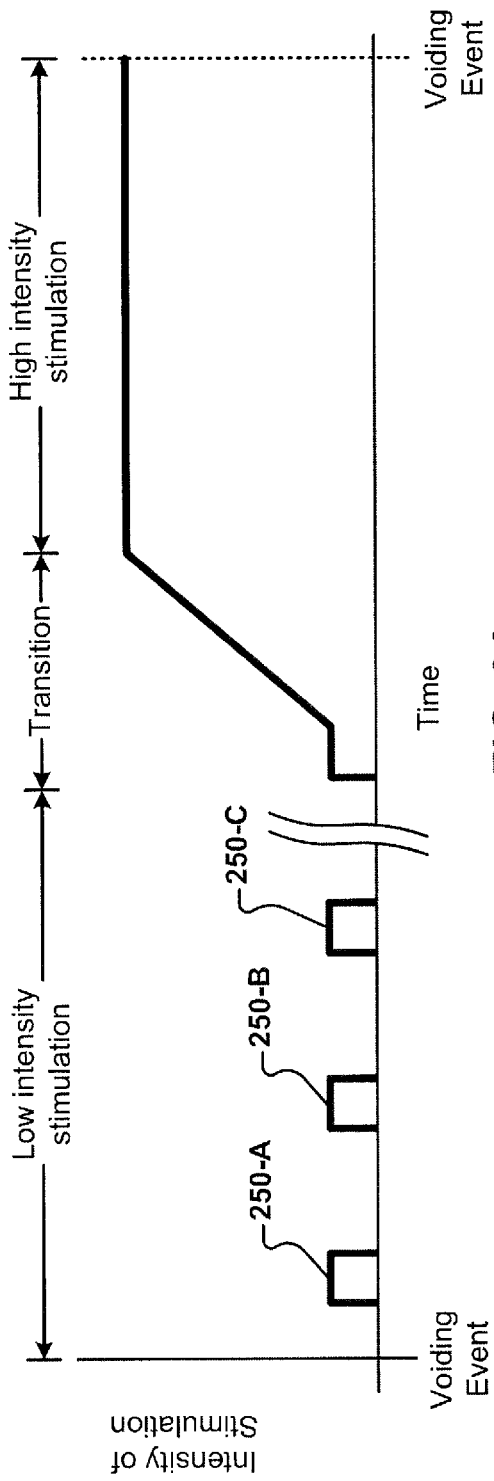
FIG. 9A is a graph illustrating an example time course for delivery of stimulation, which includes application of low intensity stimulation in pulses followed by an increase in the intensity level of stimulation to a high intensity.

Referring now to FIG. 9A, example electrical stimulation delivered by IMD 16 during a micturition cycle is shown. The graph indicates intensity of stimulation versus time. According to FIG. 9A, IMD 16 may deliver low intensity stimulation during predetermined stimulation periods, illustrated as 250-A, 250-B, and 250-C, which are each separated in time by a predetermined interval. Although the predetermined stimulation periods 250-A, 250-B, and 250-C are illustrated as single pulses in FIG. 9A, each of the stimulation periods 250-A, 250-B, and 250-C include a plurality of voltage/current pulses, the number of which depends on the pulse rate of stimulation applied.

Delivery of low intensity stimulation for a first stimulation period 250-A to patient 14 may produce a delayed response that is observed after stimulation period 250-A and persists during the period of time after stimulation period 250-A and before delivery of the low intensity stimulation during a subsequent stimulation period 250-B, which is the next stimulation period after stimulation period 250-A. Similarly, delivery of low intensity stimulation for a second stimulation period 250-B to patient 14 may produce a delayed response that is observed after stimulation period 250-B and persists during the period of time after stimulation period 250-B and before delivery of the low intensity stimulation during a subsequent stimulation period 250-C, which is the next stimulation period after stimulation period 250-C.

Figure 9B:
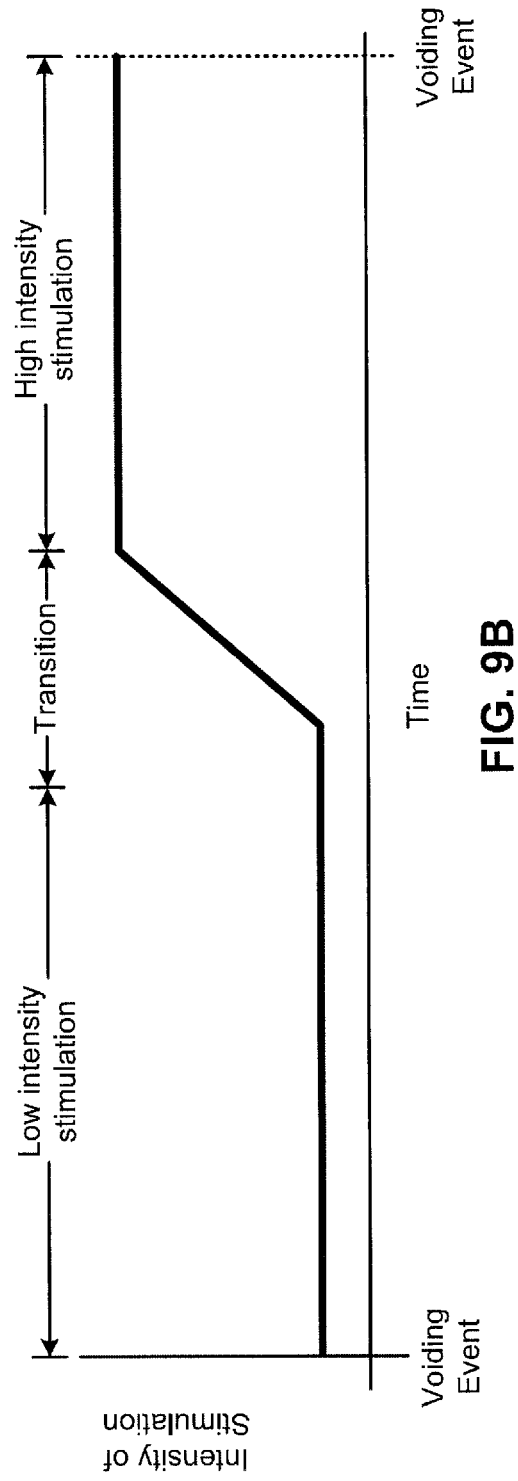
FIG. 9B is a graph illustrating another example time course for delivery of stimulation, which includes continuous application of low intensity stimulation followed by a ramping increase in the level of stimulation to a high intensity stimulation.

Durations of stimulation periods 250-A, 250-B, and 250-C, as well as the periods of time between subsequent stimulation periods 250-A, 250-B, and 250-C may be selected so that the delayed physiological response elicited by the low intensity stimulation delivered during each stimulation period helps reduce bladder contractions during the period between subsequent stimulation periods. Accordingly, in the example shown in FIG. 9A, successive stimulation periods of low intensity stimulation may be timed so that bladder contraction frequency is reduced during at time period in which electrical stimulation is not applied. In other words, the delayed response may be leveraged to produce a nearly continuous reduction in bladder contraction frequency using intermittent low intensity stimulation. The delivery of successive intervals of low intensity stimulation may result in power savings and improved battery life of IMD 16 relative to a continuous stimulation as shown in FIG. 9B. In addition, the delivery of successive intervals of low intensity stimulation may help reduce adaptation of patient 14 to the therapy delivery.

In the example therapy cycle shown in FIG. 9B, IMD 16 continuously delivers low intensity stimulation for a period of time. The low intensity stimulation and the period for which the low intensity stimulation is delivered may be defined by the low intensity stimulation parameters 220. IMD 16 transitions intensity of stimulation from the low intensity level to the high intensity level during a transition period. The characteristics of the transition period may be defined by the transition stimulation parameters 222. For example, the transition stimulation parameters 222 corresponding to FIG. 9B may define the transition from low intensity stimulation to high intensity as a ramping function. Transition stimulation parameters 222 may include a slope value that defines the ramping function. For example, the slope value may indicate an amount of intensity to increase per unit time. In one example, when IMD 16 adjusts intensity of stimulation by adjusting amplitude of stimulation, IMD 16 may increase the amplitude of stimulation per unit time in order to increase the intensity per unit time. Accordingly, in one example, IMD 16 may increase stimulation intensity per unit time during the transition period based on transition stimulation parameters 222 that define an increase in the amplitude of stimulation per unit time.

IMD 16 may deliver stimulation during the transition period based on transition stimulation parameters 222 (e.g., the slope value). Accordingly, IMD 16 may increase the intensity of stimulation from the low intensity level to the high intensity level by a predetermined amount over a predetermined duration of time. Subsequent to the transition from low intensity to high intensity, IMD 16 may deliver high intensity stimulation until a subsequent voiding event, at which time IMD 16 may restart the therapy cycle shown in FIG. 9B or modify the therapy cycle shown in FIG. 9B, as described in further detail below with respect to FIGS. 13A-13C. IMD 16 may deliver the high intensity stimulation according to the high intensity stimulation parameters 224.

Although IMD 16 is described above as delivering low intensity stimulation for a predetermined period until the transition period, IMD 16 may determine when to transition from the low intensity stimulation to the high intensity stimulation based on sensor data and/or patient input. For example, IMD 16 may transition from low intensity to high intensity based on patient input and/or sensor data that indicates an increased urge to void, a leakage episode, or another event that may indicate the efficacy of the low intensity stimulation delivered by IMD 16 may not be effective in minimizing the possibility of the occurrence of a voiding event.

As shown with respect to FIG. 9B, processor 50 of IMD 16 controls therapy delivery module 52 to modify the intensity of stimulation delivered during the transition period based on a predetermined slope (e.g., stored by memory 56 of IMD 16 or a memory of another device). In other examples, IMD 16 may modify stimulation during the transition period based on a function other than a predetermined slope. For example, IMD 16 may increase the predetermined slope of the transition period by increasing an intensity of stimulation per unit time. Alternatively, IMD 16 may decrease the slope of the transition period or rate limit the increase of intensity per unit time. IMD 16 may modify the slope of the transition period based on sensor data and/or patient input. For example, IMD 16 may increase the slope of the transition period based on sensor data and/or patient input that indicates an increase in urge to void by patient 14, a leakage episode, or another event that may indicate the efficacy of the low intensity stimulation delivered by IMD 16 may not be effective in minimizing the possibility of the occurrence of a voiding event. IMD 16 may decrease or rate limit the slope of the transition period in response to sensor data and/or patient input that indicates a reduced urge felt by patient 14 or an increase in discomfort felt by patient 14 in response to stimulation. The decrease in the slope of the transition period may provide increased patient comfort and an increase in battery life of IMD 16.

Figure 10A:
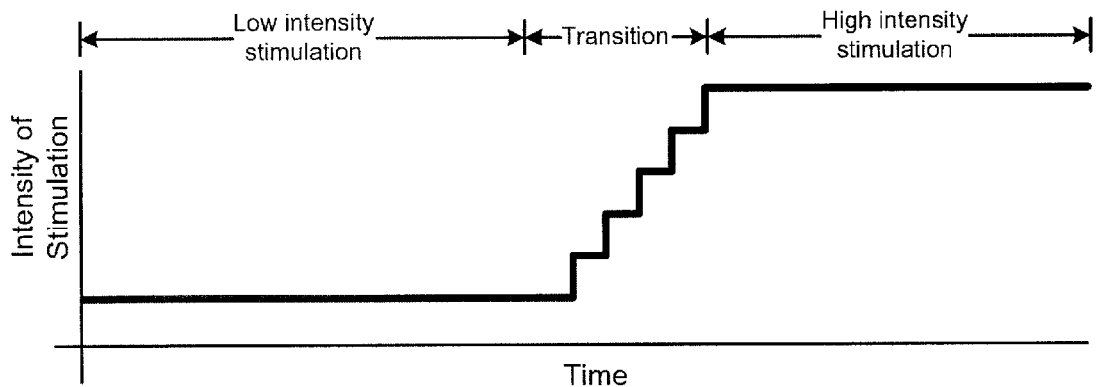
FIG. 10A is a graph illustrating another example time course for delivery of stimulation, which includes continuous application of low intensity stimulation followed by a stepping increase in the level of stimulation to a high intensity stimulation.
Figure 10B:
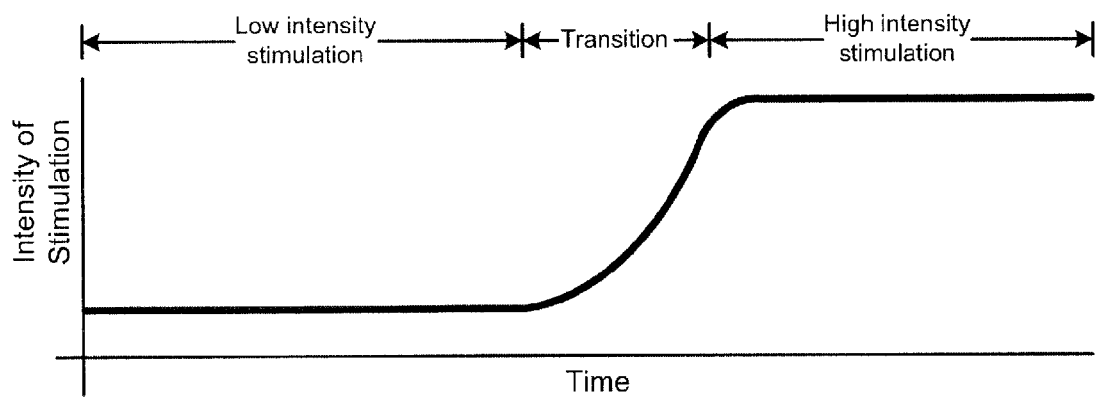
FIG. 10B is a graph illustrating another example time course for delivery of stimulation, which includes continuous application of low intensity stimulation followed by a curvilinear increase in the level of stimulation to a high intensity stimulation.
Figure 10C:
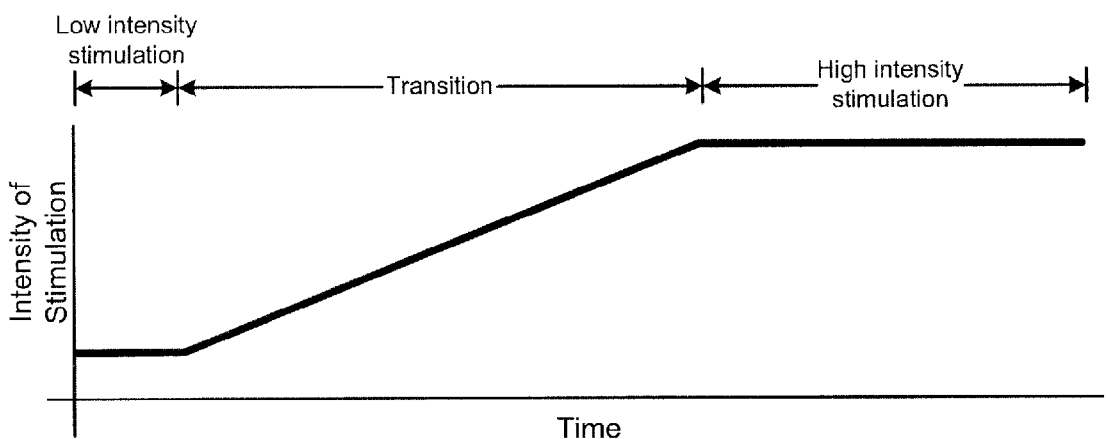
FIG. 10C is a graph illustrating another example time course for delivery of stimulation, which includes a relatively short continuous application of low intensity stimulation followed by a relatively long ramp in the level of stimulation to a high intensity stimulation.

Various types of example transition periods are shown in FIGS. 10A-10C. FIG. 10A illustrates a transition period in which IMD 16 gradually increases intensity from low intensity to high intensity using a stepping function. The rate of increase from the low intensity to the high intensity may be defined by transition stimulation parameters 222 based on at least one of a magnitude of each step in intensity and a duration of each step. Additionally, or alternatively, transition stimulation parameters 222 may define the stepping function in terms of at least one of a total length of the transition period, a total number of steps in the transition period, or a predetermined step size. Processor 50 of IMD 16 may vary any of the transition stimulation parameters 222 that define the stepping function to increase a rate at which electrical stimulation is increased from low intensity to the high intensity. Additionally, IMD 16 may vary any of the transition stimulation parameters 222 that define the stepping function to limit or reduce the rate at which electrical stimulation is increased from low intensity to high intensity. Reducing the rate at which electrical stimulation is increased from low intensity to high intensity may help reduce the possibility that patient 14 may perceive the transition or the possibility that the transition may cause discomfort to patient 14.

FIG. 10B illustrates a curvilinear increase in intensity from the low intensity to the high intensity stimulation. Accordingly, transition stimulation parameters 222 may define the transition from the low intensity to the high intensity stimulation based on a curvilinear function. In one example, the curvilinear function may be a power function. When the transition period is defined in terms of a function, processor 50 of IMD 16 may control therapy delivery module 52 to modify intensity of the transition period by modifying the function. In one example, processor 50 of IMD 16 may control therapy delivery module 52 to modify an exponent of the power function to change the rate of increase during the transition period, when the transition is defined by the power function.

FIG. 10C illustrates a relatively long transition period relative to the duration of the low intensity stimulation. In other words, FIG. 10C illustrates a scenario in which IMD 16 delivers a relatively short duration of low intensity stimulation followed by a relatively long ramping transition to the high intensity stimulation. The relatively long transition period including the relatively shallow sloped ramp may provide a more gradual increase in stimulation and a corresponding gradual decrease in the time for the stimulation delivery to elicit a physiological response that reduces bladder contraction frequency. Algorithms described hereinafter provide examples of methods that may be implemented by IMD 16 in order to vary intensities and durations of stimulation based on sensor data and/or patient input in order to adapt stimulation to patient 14.

Figure 11:
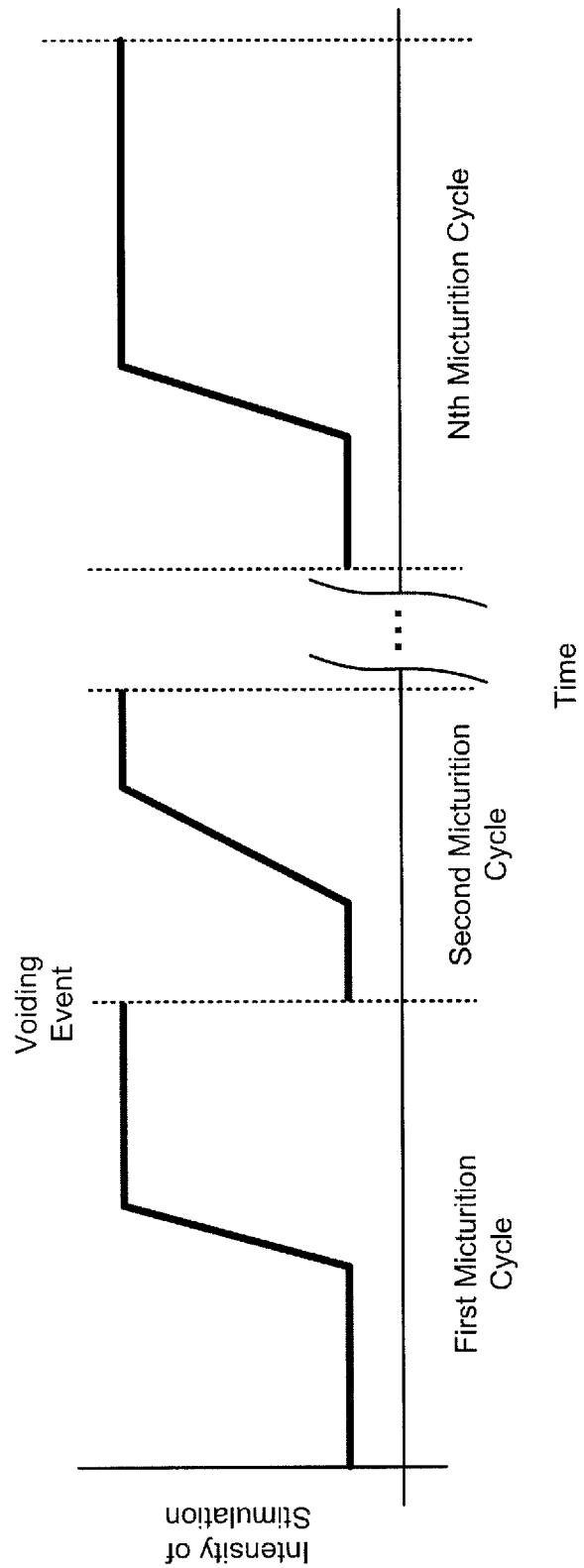
FIG. 11 is a graph illustrating modifications to the durations of low intensity stimulation, high intensity stimulation, and the transition between the low and high intensities based on micturition cycles of a patient.

FIG. 11 illustrates a series of example therapy cycles that may be applied by IMD 16 during consecutive micturition cycles when IMD 16 is configured to adapt electrical stimulation to patient 14 based on sensor data and/or patient input. Specific adaptation algorithms that may be implemented to adapt stimulation to patient 14 are described herein with reference to FIGS. 13A-13C. The series of therapy cycles illustrated in FIG. 11 are merely an example series of possible therapy cycles with which IMD 16 may deliver therapy to patient 14 based on sensor data and/or patient input, and are meant to illustrate the concept of adaptation. For example, FIG. 11 illustrates a plurality of therapy cycles for which a duration of low intensity stimulation may vary between micturition cycles, a duration of the transition period may vary between micturition cycles, and a duration of high intensity stimulation may vary between micturition cycles. FIG. 11 also illustrates that a total duration of the low intensity stimulation, transition stimulation, and high intensity stimulation may vary between micturition cycles. IMD 16 may implement adaptation algorithms in order to determine which of the various durations should be modified between micturition cycles. Example adaptation algorithms are described with respect to FIGS. 12-13C.

Figure 12:
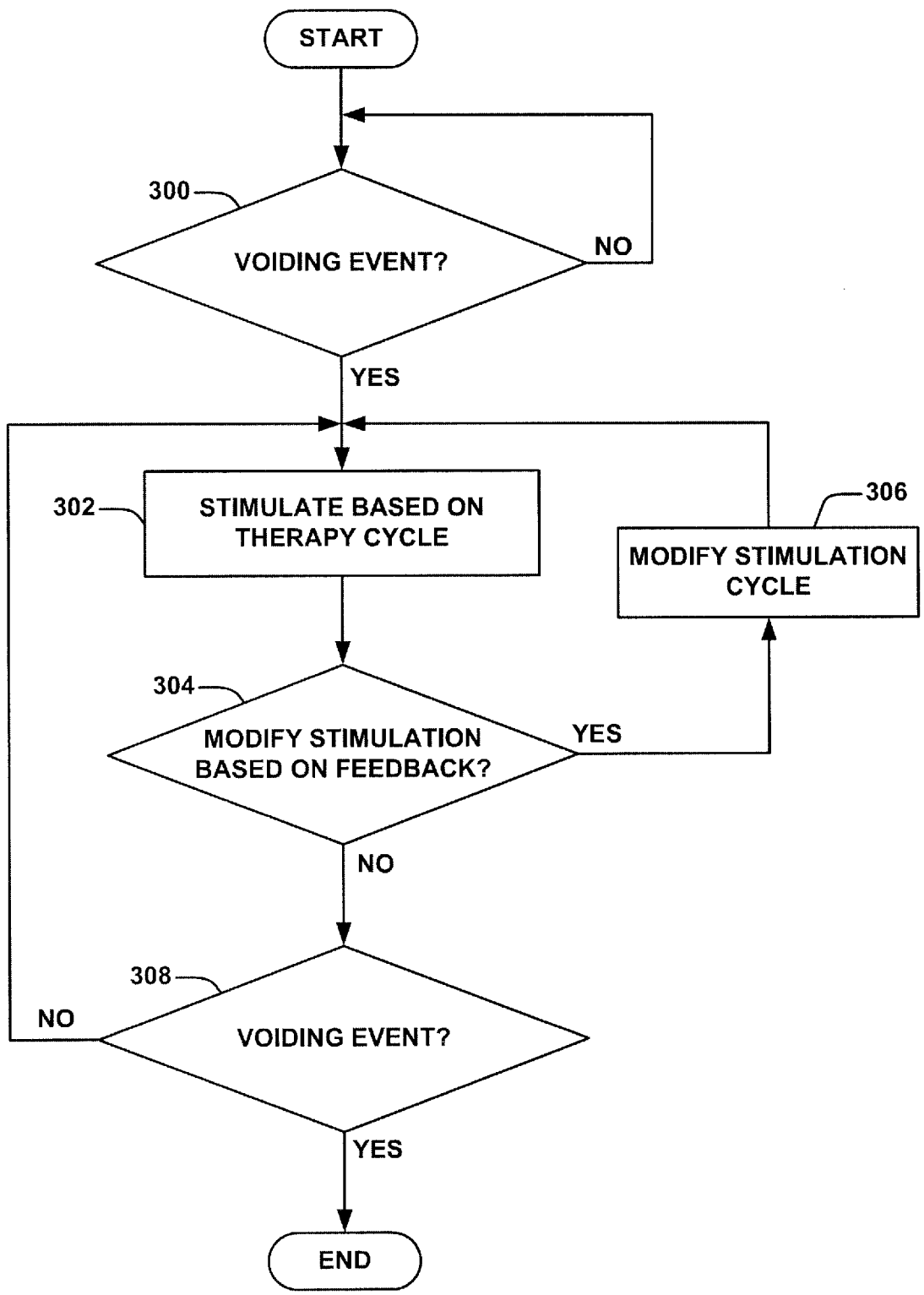
FIG. 12 is a flow diagram of an example method for adapting electrical stimulation based on sensor data and/or patient input.

FIG. 12 illustrates a method for adapting electrical stimulation based on sensor data and/or patient input. In accordance with the technique shown in FIG. 12, processor 50 of IMD 16 detects a voiding event (300). For example, as described above with respect to FIG. 7, processor 50 may detect a voiding event based on sensor data and/or patient input. Subsequent to detection of the voiding event, processor 50 controls therapy delivery module 52 to generate and deliver electrical stimulation to patient 14 to manage urgency and/or urinary incontinence based on a therapy cycle (302). For example, IMD 16 may deliver stimulation based on low intensity stimulation parameters 220, transition stimulation parameters 222, and high intensity stimulation parameters 224.

During the therapy cycle, processor 50 determines whether to modify the therapy cycle based on feedback (e.g., sensor data and/or patient input) (304). If processor 50 determines that the therapy cycle should be modified, processor 50 modifies the therapy cycle (306) (e.g., in real-time) and proceeds to control therapy delivery module 52 to generate and deliver stimulation to patient 14 based on the modified therapy cycle. Processor 50 may determine that a modification to a therapy cycle is desirable if, for example, processor 50 receives input from patient 14, sensor 22 or another patient parameter sensor that indicates that patient 14 experienced an urge to void, a leakage episode, or another event that indicates a less than desirable level of efficacy of the low intensity stimulation.

For example, if processor 50 detects an imminent involuntary voiding event earlier than was expected (e.g., prior to finishing delivery of low intensity stimulation according to the current therapy cycle) while providing low intensity stimulation, IMD 16 may deliver an immediate real-time increase in stimulation intensity. Processor 50 may then subsequently modify the therapy cycle to provide the increase in stimulation intensity earlier in the micturition cycle for following micturition cycles. If IMD 16 determines a modification is not necessary, e.g., because of a lack of patient or sensor input that indicates the low intensity stimulation is not efficacious, then IMD 16 may continue to stimulate based the therapy cycle until a subsequent voiding event is detected (308). For example, after the predetermined time period since the last voiding event expires, processor 50 of IMD 16 may control therapy control module 52 to increase the stimulation intensity to the high intensity level via a transition period in which intermediate levels of stimulation intensity are delivered to patient 14. Thereafter, processor 50 may control therapy control module 52 to deliver high intensity stimulation until detection of a subsequent voiding event. Upon detection of the subsequent voiding event, IMD 16 may restart the therapy cycle and deliver low intensity stimulation. In this way, a voiding event indicates the start of a new therapy cycle that has substantially the same duration as a micturition cycle of patient 14.

Figure 13A:
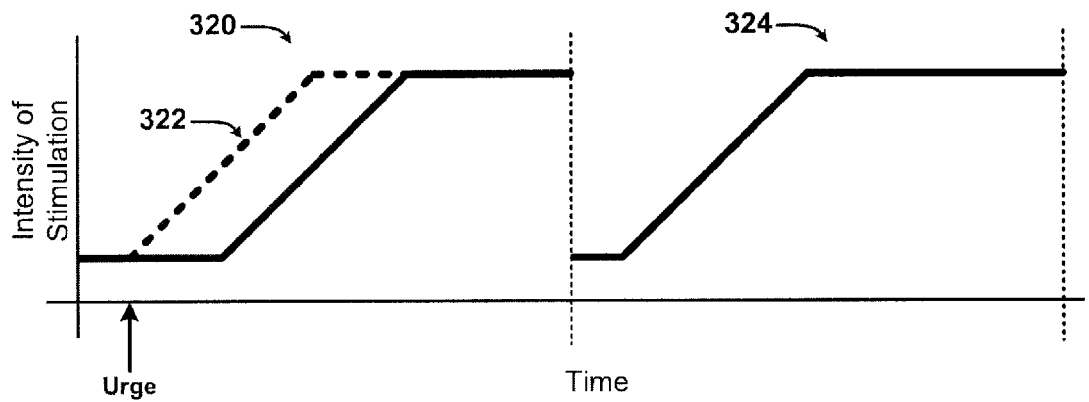
FIG. 13A is a graph illustrating the modification of the duration of low intensity stimulation based on micturition cycles of a patient.
Figure 13B:
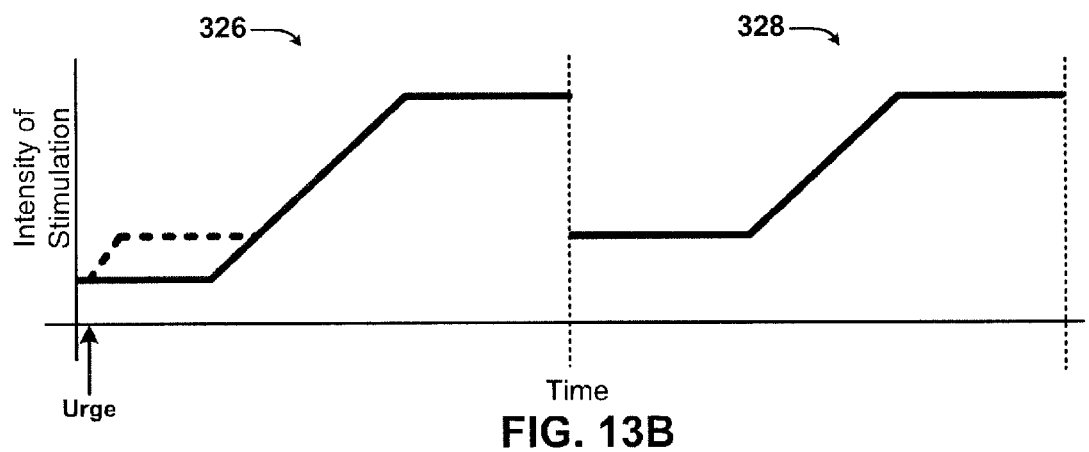
FIG. 13B is a graph illustrating the modification of the intensity of stimulation in response to input indicative of a voiding event or a voiding condition.
Figure 13C:
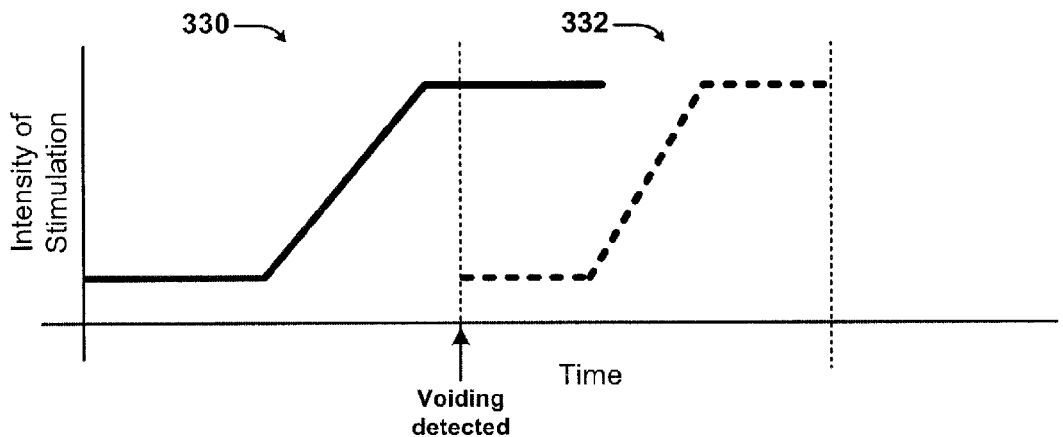
FIG. 13C is a graph that illustrates modification of the total duration of stimulation delivery during a micturition cycle.

FIGS. 13A-13C illustrate example therapy cycles, which are used to describe example algorithms that may be implemented by IMD 16 to adapt the low intensity stimulation parameters 220, transition stimulation parameters 222, and high intensity stimulation parameters 224 based on sensor data and/or patient input. In other words, FIGS. 13A-13C illustrate that IMD 16 may adapt the intensity and duration of stimulation based on sensor data and/or patient input received during prior micturition cycles. The solid lines in the first micturition cycles illustrated in FIGS. 13A-13C may indicate an expected therapy cycle at the start of the first micturition cycle. Accordingly, the solid lines may indicate a therapy cycle stored in memory 56 of IMD 16 at the start of the first micturition cycle. The dotted lines in FIGS. 13A-13C illustrate a modification to a stored therapy cycle implemented by processor 50 of IMD 16 based on sensor data and/or patient input, e.g., indicating an increase in urge to void, a leakage episode or a voiding event. While input indicating an urge to void is described with respect to FIGS. 13A-13C, in other examples, other types of input may cause the therapy cycle to be modified. Further, while the modification to the therapy cycle is described as being performed by processor 50 of IMD 16, in other examples, a processor of another device (e.g., programmer 24) may control IMD 16 to modify a therapy cycle.

FIG. 13A illustrates adaptation of the duration of low intensity stimulation between micturition cycles. During the first micturition cycle 320 shown in FIG. 13A, the stored therapy cycle was configured to deliver the low intensity stimulation to patient 14 for a predetermined period of time. However, processor 50 detects an urge to void before the end of the predetermined period of time, and in response, processor 50 controls therapy delivery module 52 to enter the transition period 322 earlier than originally defined by the stored therapy cycle in order to deliver a higher intensity stimulation that may better reduce the detected urge to void. The dotted line may indicate a real-time modification to the delivery cycle that was implemented by processor 50 to adapt the therapy cycle to compensate for the detected urge. The occurrence of the urge to void may indicate, for example, that the stored therapy cycle was not efficacious, e.g., because the patient condition has changed or because of an electrode or other therapy delivery hardware condition (e.g., tissue ingrowth around an electrode may change the intensity of stimulation actually delivered to tissue, migration of a lead and respective electrodes from a target tissue site, an impedance change to an electrode, and the like). In this way, processor 50 may adapt the therapy cycle to accommodate real-time changes to the patient condition or therapy system.

In some examples, processor 50 stores the parameter values that define the modified therapy cycle in memory 56 of IMD 16 or a memory of another device. During a second micturition cycle 324 shown in FIG. 13A, processor 50 controls therapy delivery module 52 to generate and deliver therapy to patient 14 based on the modified therapy cycle generated during the prior micturition cycle. For example, processor 50 may have updated the low intensity stimulation parameters 220 to provide for a shorter low intensity stimulation duration since sensor data and/or patient input in the prior micturition cycle indicated that shorter low intensity durations may be desirable for patient 14.

FIG. 13B illustrates another example in which the intensity of stimulation is adapted in response to sensor data and/or patient input. During the first micturition cycle 326 shown in FIG. 13B, the stored therapy cycle was configured to deliver the low intensity stimulation to patient 14 for a predetermined period of time. However, as shown in FIG. 13B, processor 50 detects an urge to void by patient 14 before the end of the predicted low intensity stimulation. In response to detecting the urge to void, processor 50 controls therapy delivery module 52 to increase stimulation intensity earlier than that indicated by the therapy cycle in order to adapt the stimulation to better address the detected urge to void.

The dotted line may indicate the response of IMD 16 to the detected urge in real-time. In the example shown in FIG. 13B, rather than modifying the duration of the low intensity stimulation as in the example shown in FIG. 13A, processor 50 modifies the amplitude of the low intensity stimulation in response to sensor data and/or patient input indicating the urge to void. In some examples, processor 50 stores the parameter values that define the modified therapy cycle in memory 56 of IMD 16 or a memory of another device. During a second micturition cycle 328 shown in FIG. 13B, processor 50 controls therapy delivery module 52 to generate and deliver therapy to patient 14 based on the modified therapy cycle generated during the prior micturition cycle. For example, processor 50 may have updated the therapy cycle to deliver an intensity of stimulation that is greater than the low intensity at the start of the first micturition cycle based on the sensor data and/or patient input received during the previous micturition cycle.

FIG. 13C illustrates two consecutive therapy cycles, and demonstrates the result of modifying a total duration of a therapy cycle based on user input and/or sensor input. During the first micturition cycle 330 shown in FIG. 13B, the stored therapy cycle has a total duration of time comprising the period of time in which the low intensity stimulation is delivered to patient 14, the transition period, and the period of time in which the high intensity stimulation is delivered to patient 14. Based on sensor data and/or patient input, processor 50 determines that the total duration of the micturition cycle is shorter than the duration of the stored therapy cycle. For example, processor 50 may detect the occurrence of a voiding event prior to the end of the therapy cycle (e.g., during the high intensity stimulation delivery as shown in FIG. 13C or during the low intensity stimulation delivery or the transition period). As a result of a therapy cycle that is longer than a micturition cycle, IMD 16, when delivering stimulation according to the stored therapy cycle, may deliver stimulation at too low of an intensity level to be effective in minimizing the occurrence of an involuntary voiding event due to the filling of bladder 12 faster than expected.

In response to the detection of the voiding event during delivery of the high intensity stimulation, processor 50 may modify the new durations for each of the low intensity, the transition period, and the high intensity. For example, IMD 16 shortened each of the durations proportionally as illustrated by the dotted line indicating the adapted stimulation delivered during the second micturition cycle 332. In some examples, processor 50 stores the parameter values that define the modified therapy cycle in memory 56 of IMD 16 or a memory of another device. During a third micturition cycle that follows the second micturition cycle 332 shown in FIG. 13C, processor 50 may control therapy delivery module 52 to generate and deliver therapy to patient 14 based on the shortened therapy cycle.

Figure 14:
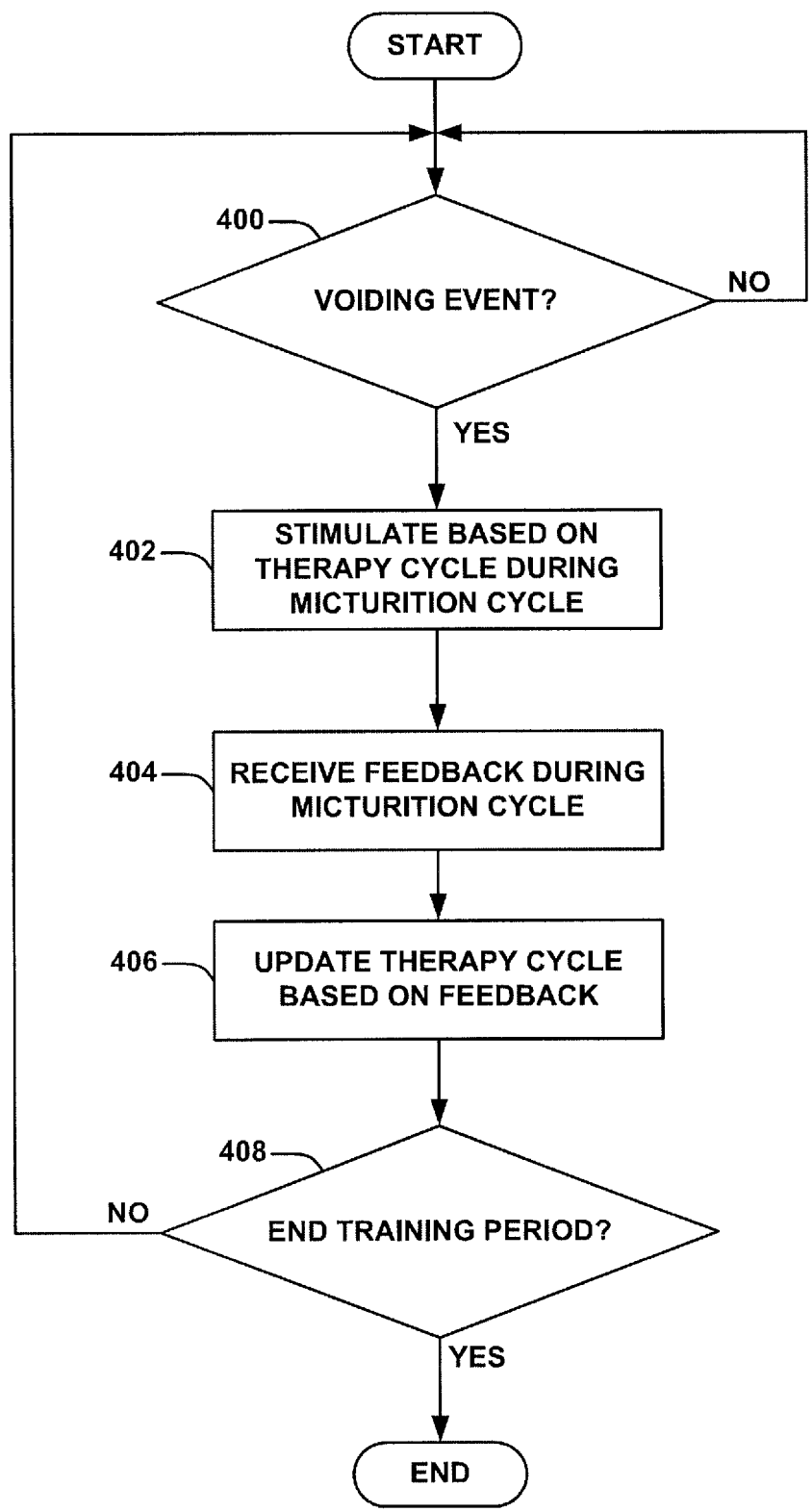
FIG. 14 is a flow diagram of an example method for adapting a therapy cycle during a training period according to patient input and/or sensor data.

FIG. 14 illustrates an example method for adapting a therapy cycle during a training period according to patient input and/or sensor data. Processor 50 detects a voiding event (400), e.g., as described above with respect to FIG. 7. Processor 50 controls therapy delivery module 52 to generate and deliver electrical stimulation according to a therapy cycle during a micturition cycle (402). For example, IMD 16 may deliver electrical stimulation based on low intensity stimulation parameters 220, transition stimulation parameters 222, and high intensity stimulation parameters 224 during the micturition cycle.

During the micturition cycle, IMD 16 receives patient input and/or sensor data (404). For example, patient input may include values that indicate an amount of fluid intake by the patient, an urge felt by the patient, a leakage incident experienced by the patient, an imminent voiding event predicted by the patient, or a voluntary voiding event undertaken by the patient. Sensor data may include, for example, signals that indicate bladder impedance, bladder pressure, pudendal or sacral afferent nerve signals, or a urinary sphincter EMG. IMD 16 updates the therapy cycle based on the patient input and/or sensor data (406), e.g., as described above with respect to FIGS. 13A-13C.

Processor 50 determines whether the training period has ended (408). For example, IMD 16 may determine that the training period has ended based on a number of micturition cycles for which the training period was run, based on a duration of time (e.g., days, months, etc.) for which the training period was run, etc. After the end of the training period, the therapy cycle may be considered adapted for future use with patient 14. Accordingly, after the training period, IMD 16 may deliver effective stimulation that varies according to patient specific parameters with or without sensor data and/or patient input.

In addition to the parameters mentioned above, IMD 16 may adapt the therapy cycle based on other parameters that may be relevant to predicting micturition cycles of patient 14. For example, IMD 16 may adapt the therapy cycle based on a time of day corresponding to the stimulation. In one example, IMD 16 may reduce intensity of stimulation during the night when patient 14 is sleeping, during which time some patients may be less prone to involuntary voiding events.

In other adaptation examples, IMD 16 may adapt the therapy cycle based on parameters relating to a mean, median, shortest, or longest duration between prior voiding events, and, in some examples, based on the time of day of prior voiding events. For example, based on historical data gathered during a learning phase that precedes implementation of IMD 16 to deliver therapy, IMD 16 may determine the duration of future therapy cycles based on the mean or median duration of therapy cycles in the past. Processor 50 of IMD 16 may also learn, for example, expected times of voiding events, which may be useful if patient 14 voids at substantially regular times during a particular day. During chronic therapy delivery, after the learning phase, processor 50 of IMD 16 may control therapy delivery module 52 to restart a therapy cycle (e.g., transition from the high intensity stimulation to the low intensity stimulation) at predetermined times of the day, which may be determined based on the learning phase and the patient's pattern of voiding during the learning phase.

Although therapy cycles described above are initiated using low intensity stimulation, then transition from the low intensity stimulation to the high intensity stimulation, IMD 16 may deliver stimulation according to other therapy cycles. For example, IMD 16 may initially deliver high intensity stimulation at the start of a micturition cycle then transition to a lower intensity stimulation (e.g., low intensity stimulation) later in the micturition cycle. As a further example, IMD 16 may include a plurality of transition periods that transition between a plurality of intensity levels during a micturition cycle. For example, IMD 16 may deliver stimulation at a low intensity level, then transition to a high intensity level, then later transition to a lower intensity level. Accordingly, the therapy cycles described above are merely examples. A dynamic adjustment of stimulation intensity levels may help prevent adaptation of the patient to the therapy delivery while still maintaining the efficacy of stimulation.

Figure 15:
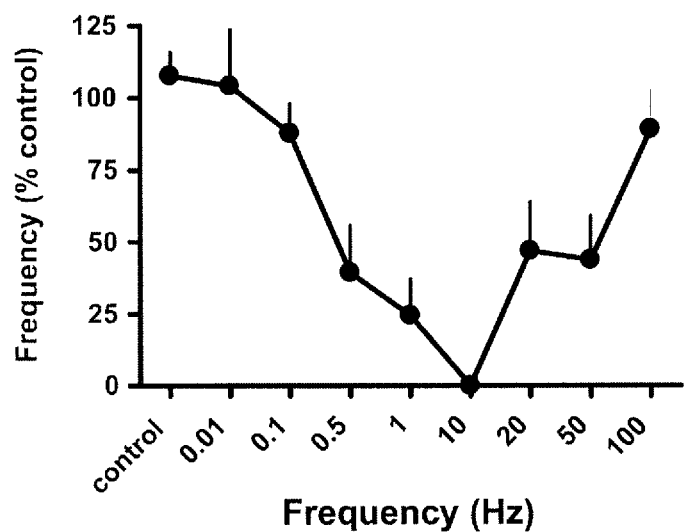
FIG. 15 is a graph that illustrates a relationship between electrical stimulation frequency and bladder contraction frequency in a rat test subject.
Figure 16:
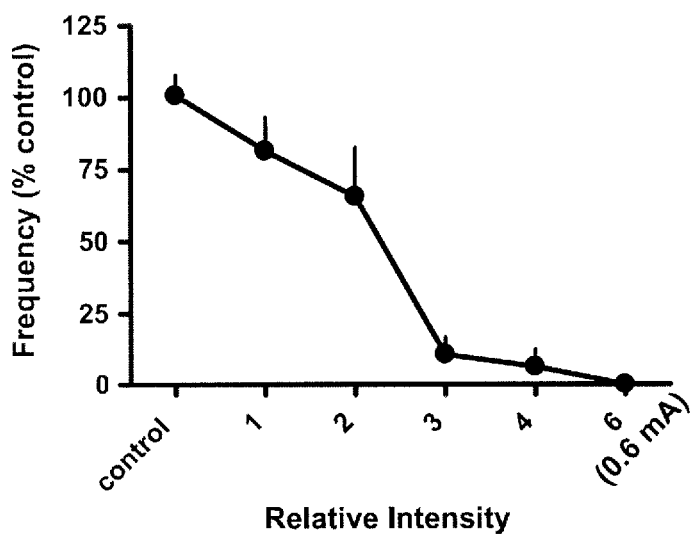
FIG. 16 is a graph that illustrates a relationship between relative intensity of electrical stimulation and bladder contraction frequency in a rat test subject.
Figure 17:
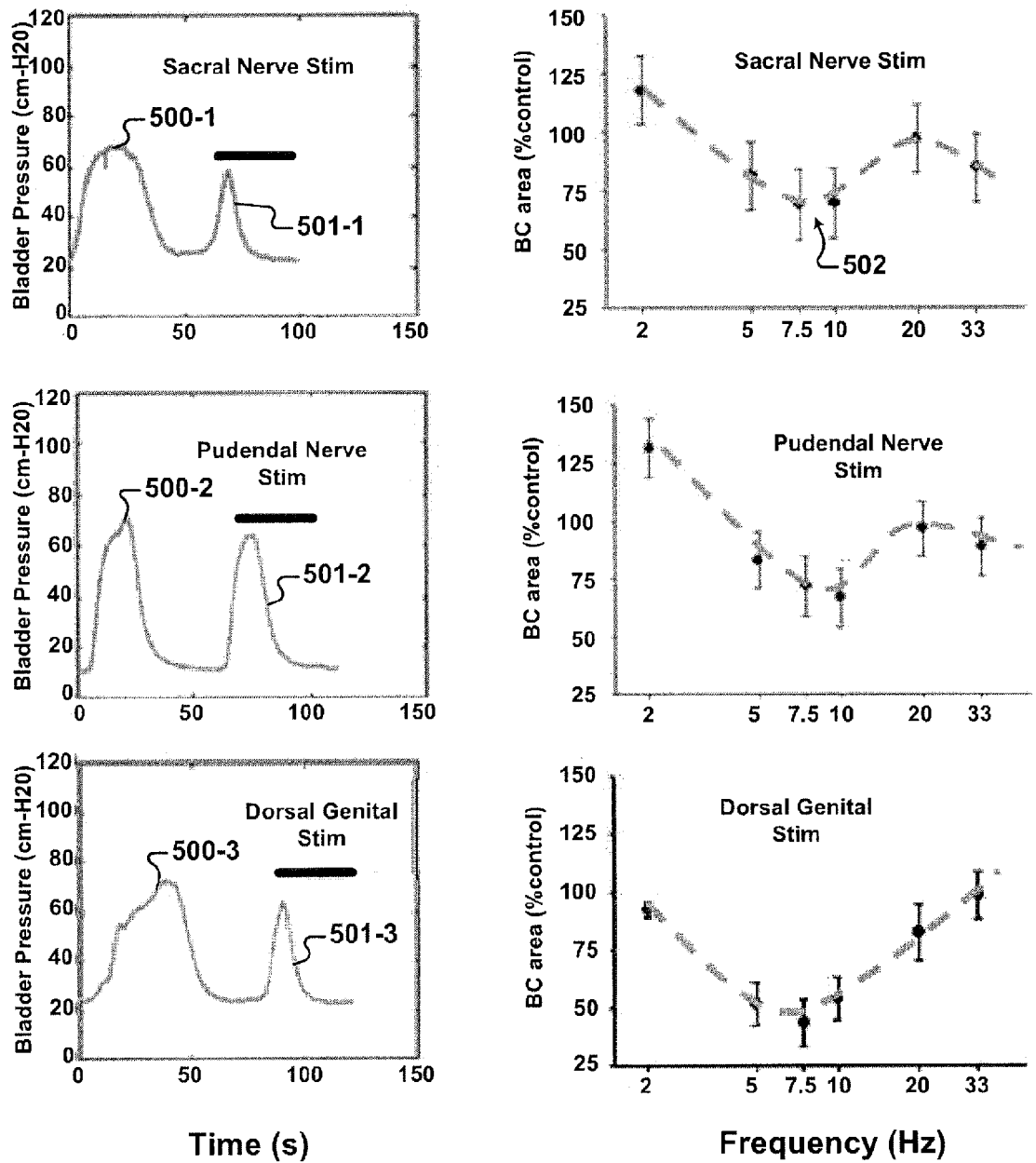
FIG. 17 is a graph that illustrates relationships between electrical stimulation frequency and bladder contraction in a feline test subject.
Figure 18A:
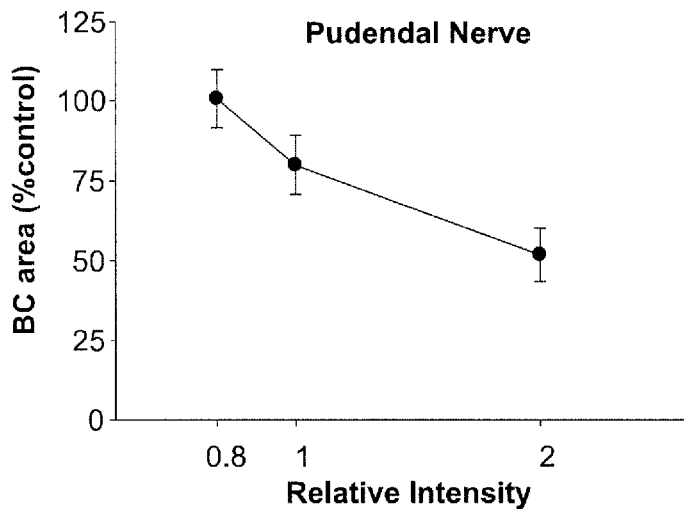
FIGS. 18A-18C are graphs that illustrate relationships between a relative intensity of electrical stimulation and bladder contraction in a feline test subject.
Figure 18B:
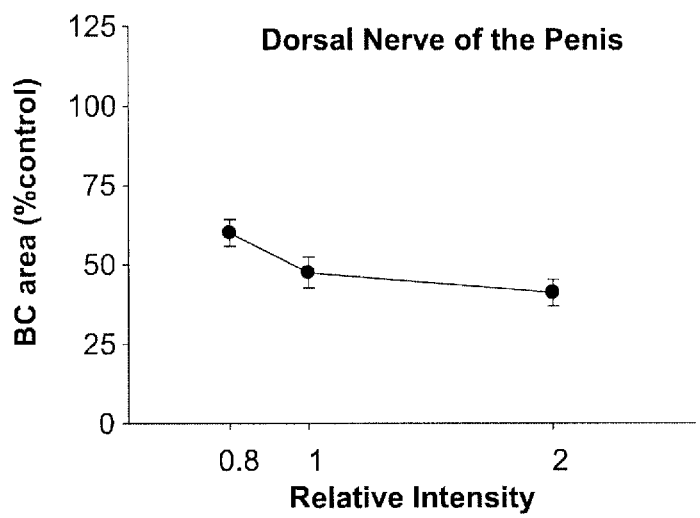
Figure 18C:
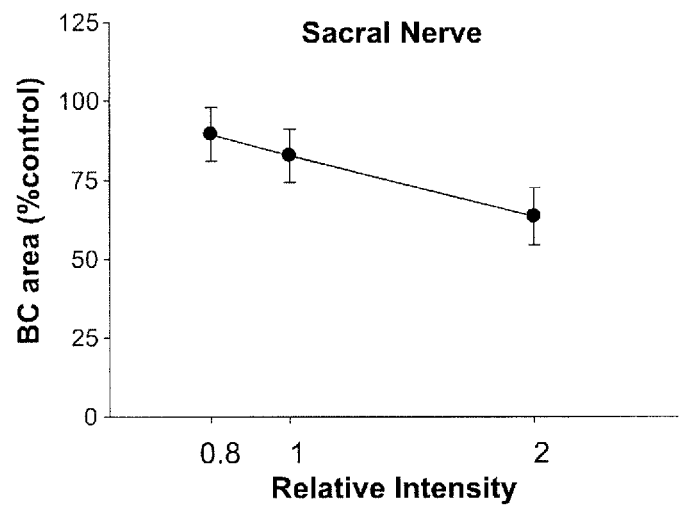

FIG. 15 illustrates a relationship between electrical stimulation frequency and the bladder contraction frequency in a rat test subject. FIG. 16 illustrates a relationship between a relative intensity of electrical stimulation and bladder contraction frequency in a rat test subject. FIG. 17 illustrates relationships between electrical stimulation frequency and bladder contraction in a feline test subject. FIGS. 18A-18C illustrate relationships between a relative intensity of electrical stimulation and bladder contraction in a feline test subject.

FIG. 15 is a graph that illustrates a change in bladder contraction frequency of a rat test subject in response to spinal nerve (e.g., L6) electrical stimulation delivered to the rat test subject. In order to obtain the experimental data shown in FIG. 15, bladder contractions of one or more rat test subjects were observed while applying electrical stimulation over a range of electrical stimulation frequencies (e.g., 0-100 Hz). The stimulation was delivered using biphasic pulses having pulse width of approximately 0.1 ms.

The dependent axis labeled "Frequency (% control)" indicates a frequency of bladder contractions during electrical stimulation relative to the frequency of bladder contractions before electrical stimulation was applied. In order to determine the "Frequency (% control)," bladder contraction frequencies during electrical stimulation were normalized by dividing bladder contraction frequencies during electrical stimulation by a control frequency for the rat test subject, the control frequency being the bladder contraction frequency observed prior to delivery of any electrical stimulation.

For the particular test subject used to generate the results shown in FIG. 15, electrical stimulation at approximately 10 Hz may be referred to as a relatively high intensity stimulation because a maximum attenuation (i.e., to approximately 0) of bladder contraction frequency occurred when electrical stimulation was approximately 10 Hz. FIG. 15 further illustrates that bladder contraction frequency may be less attenuated by electrical stimulation that deviates from a frequency of approximately 10 Hz. For example, the test results in FIG. 15 indicate that a decrease in stimulation frequency from a relatively high intensity at approximately 10 Hz towards a stimulation frequency of 0.01 Hz may result in a decrease in the attenuation of bladder contraction frequency. Similarly, the test results in FIG. 15 indicate that deviation in stimulation frequency from approximately 10 Hz towards a higher frequency of 100 Hz may cause a decrease in the attenuation of bladder contraction frequency. In other words, deviation of stimulation frequency from 10 Hz towards either a higher or lower frequency may correspond to a decrease in the intensity of electrical stimulation according to the data of FIG. 15.

FIG. 16 is a graph that illustrates a change in bladder contraction frequency of a rat test subject in response to spinal nerve electrical stimulation. In order to obtain the experimental data shown in FIG. 16, bladder contractions of one or more rat test subjects were observed while applying different intensities of stimulation. A relative intensity value of 1 corresponds to a lowest amount of intensity that evoked a first, barely discernable muscle contraction from the test subject. In the example of FIG. 16, a relative intensity of 1 corresponds to an approximately 0.1 mA amplitude biphasic pulse having a frequency of approximately 10 Hz and a pulse width of approximately 0.1 ms. A relative intensity of less than 1 corresponds to a stimulation amplitude less than approximately 0.1 mA, while a relative intensity of 6 may correspond to a stimulation amplitude of approximately 0.6 mA. The data of FIG. 16 may illustrate the concept that a relatively greater intensity of electrical stimulation may cause a relatively greater attenuation of bladder contraction frequency, while a relatively lesser intensity of electrical stimulation may cause a relatively lesser attenuation of bladder contraction frequency.

Although FIGS. 15-18 are graphs that include experimental data that indicates a bladder response of rat/feline test subjects to electrical stimulation, it is believed that a similar physiological response to stimulation as that shown in FIGS. 15-18 may be applicable to human subjects.

Experimental preparation and instrumentation of the rat test subjects used for collection of data in FIGS. 15-16 is now described. The rat test subjects used for collection of data in FIGS. 5-6 were prepared and instrumented in a similar manner. The data of FIG. 5 was collected from two different rat test subjects. The data of FIG. 6 is summarized data from 30 rat test subjects, 13 without stimulation, 7 with high intensity stimulation, and 10 with low intensity stimulation. The data of FIG. 15 and FIG. 16 was collected from 66 and 54 different rat test subjects, respectively.

The rat test subjects were female Sprague-Dawley rats weighing approximately 200 grams (g) to approximately 300 g. The rat subjects were anesthetized with urethane using two intraperitoneal injections, approximately 4 minutes apart, for a total dosage of approximately 1.2 grams/kilogram. To record bladder contractions, a cannula (a PE 50—polyethylene cannula, e.g., having a 0.58 mm inner diameter) was placed into the bladder of each test subject via the urethra which was ligated to create an isovolumetric bladder. The urethral cannula was connected via a T-type connector (e.g., a three terminal connector) to a low volume pressure transducer of a data acquisition system. The other end of the T-type connector was linked to a 20 cubic centimeter (cc) syringe with a perfusion pump.

To deliver electrical stimulation, a wire electrode was placed bilaterally under the L6 spinal nerve of the test subject. The dorsal skin around the sacral and thoracic surface of the test subject was shaved and a dorsal midline incision was made from approximately spinal nerve L3 to S2. The L6/S1 posterior processes were exposed. The S1 processes were removed and the L6 nerve trunks localized caudal and medial to the sacroiliac junction. After the wire electrode was placed under each nerve with two bared portions of Teflon-coated, 40-guage, stainless steel wire, silicone adhesive was applied to cover the wire around the nerve, and sutured shut. The wire electrode was connected to a stimulus isolator (an SIU-V Grass Medical Instruments Stimulus Isolation Unit available from Astro-Med, Inc of West Warwick, R.I.) with a Grass S88 stimulator. A needle electrode under the skin of the tail of the test subject served as the ground. The stimulator generated pulses to both nerves serially.

To induce rhythmic bladder contractions, saline was infused into the bladder of the test subject at a rate of approximately 50 microliters per minute (µL/minute) to induce a micturition reflex (defined here as bladder contraction with intensity >10 millimeters of mercury (mmHg)). The infusion rate was then lowered to approximately 10 µL per minute until 3-5 consecutive contractions were established. Infusion was then terminated. After an approximately 15 minute control period, nerve stimulation was applied for about 10 minutes and the bladder rhythmic contraction was recorded for approximately 20 minutes post stimulation. Two parameters of BRC were evaluated: frequency/interval and amplitude. Biphasic pulses (pulse width of approximately 0.1 ms) of different intensities, $T_{mot}$–$6*T_{mot}$, were used to stimulate the spinal nerve at frequencies ranging from approximately 0.01 Hz to approximately 100 Hz. $T_{mot}$ was defined as the lowest intensity to evoke the first, barely discernable muscle contraction. Any rat subject with $T_{mot}$ over 0.4 mA was excluded from the study.

Experimental preparation and instrumentation of feline subjects used for collection of data in FIGS. 17-18 is now described. The data for FIGS. 17-18 was collected from 8 feline subjects for a total of 909 test trials and 842 control trials. Data for pudendal nerve stimulation was collected from 6 feline subjects for a total of 288 test trials. Data for the S1 sacral nerve was collected from 5 feline subjects for a total of 270 test trials. Data for the dorsal nerve of the penis was collected from 8 feline subjects for a total of 351 trials.

Each feline subject was initially anesthetized with ketamine hydrochloride (HCl) (approximately 25-35 milligrams per kilograms (mg/kg) of the subject's weight, intramuscular), and a venous catheter was inserted in the cephalic vein. Anesthesia was maintained with alpha-chloralose (approximately 60 mg/kg IV, supplemented at approximately 15 mg/kg).

Each animal was instrumented to record bladder pressure and electromyogram (EMG) from the external anal sphincter (EAS). The bladder was cannulated through the urethra with a five French (5F) catheter that allowed control of bladder volume and measurement of bladder pressure, and the urethra was obstructed to maintain isovolumetric conditions. Pressure signals were amplified, low pass filtered at 100 Hz, and digitized for off-line analysis. EMGs from the EAS were recorded with bipolar fine wire intramuscular electrodes, amplified, filtered at 10 Hz-1 kHz, and displayed. The S1 sacral nerve (feline homologue of the human S3 sacral nerve) and compound pudendal nerve were exposed and instrumented with bipolar nerve cuff electrodes, and a percutaneous wire electrode was inserted into the penile body with a hypodermic needle for stimulation of the dorsal nerve of the penis.

Isovolumetric distention evoked reflex bladder contractions generated by filling the bladder with warm saline while obstructing the urethra with the catheter. Bladder contractions were maintained through injection and withdrawal of small amounts of fluid (approximately 1 cc). The effects of stimulation on reflex bladder contractions were evaluated with a randomized block design, with stimulation intensity, frequency, and stimulation location randomized within individual blocks. Stimuli were approximately 30 second trains of regulated current. Approximately 100 microseconds (µs) per phase biphasic pulses were delivered across a range of frequencies (approximately 2 Hz, 5 Hz, 7.5 Hz, 10 Hz, 20 Hz, and 30 Hz) and amplitudes (approximately 0.8, 1.0, and 2.0 times the threshold to evoke reflex activity in the EAS).

The graphs of bladder pressure vs. time on the left side of FIG. 17 show example stimulation runs. Each stimulation run includes a portion (500-1, 500-2, 500-3) in which bladder contractions were measured without application of electrical stimulation to the test subject. Each stimulation run also includes a subsequent portion (501-1, 501-2, 501-3) in which electrical stimulation was applied upon detection of bladder contraction. Each of the graphs on the left side of FIG. 17 show that bladder contractions were attenuated upon delivery of electrical stimulation. The amount of attenuation was quantified by comparing the areas under the curves when no stimulation was applied to the areas under the curves when stimulation was applied. In other words, the areas under the portions 500-1, 500-2, 500-3 were compared to areas under the portions 501-1, 501-2, 501-3, respectively. In each case, the areas under the curves were reduced as a result of stimulation.

The graphs on the right side of FIG. 17 show data for a plurality of stimulation runs, as described above, using various stimulation parameters. The graphs on the right side of FIG. 17 include data from stimulation runs conducted in a manner similar to that illustrated on the left side of FIG. 17. The graphs on the right side show a change in bladder control (BC) area for stimulation runs based on a frequency of stimulation applied. Specifically, a plurality of stimulation runs were performed for each frequency of stimulation (approximately 2 Hz, 5 Hz, 7.5 Hz, 10 Hz, 20 Hz, and 33 Hz) while the change in area on the bladder pressure curve was measured.

Each of the graphs on the right side of FIG. 17 show that for the test subjects, a maximum reduction in bladder contraction area occurred in the range of approximately 5 Hz-approximately 10 Hz. For example, the top graph shows that bladder contraction area was reduced to approximately 75% of the bladder contraction area present without stimulation, as indicated at 502. The areas of the graphs having minimum BC area (i.e., maximum attenuation) may correspond to high intensity stimulation. Frequencies that deviate from the minimum BC area may correspond to relatively lower intensity stimulation.

FIGS. 18A-18C show data for a plurality of stimulation runs, as described above, using various intensities of stimulation at various locations in a feline test subject. A relative intensity value of 1 corresponds to a lowest amount of intensity (e.g., lowest amount of current) that evoked a first, barely discernable muscle contraction (e.g., in the EAS) by the test subject. A relative intensity of 2 may correspond twice as much intensity (e.g., twice as much current) as a relative intensity of 1. The data of FIGS. 18A-18C may illustrate the concept that a relatively greater intensity of electrical stimulation may cause a relatively greater attenuation of bladder contraction in the feline test subject, while a relatively lesser intensity of electrical stimulation may cause a relatively lesser attenuation of bladder contraction.

The techniques described in this disclosure may be implemented in hardware, software, firmware, or any combination thereof. In particular, the techniques may be implemented in a hardware device, such as a wireless communication device or network device, either of which may include software and/or firmware to support the implementation. For portions implemented in software, the techniques may be realized in part by a computer-readable medium comprising program code containing instructions that, when executed, performs one or more of the methods described above. In this case, the computer readable medium may comprise RAM (e.g., synchronous dynamic random access memory (SDRAM)), ROM, NVRAM, EEPROM, FLASH memory, magnetic or optical data storage media, and the like.

The program code may be executed by one or more processors, such as one or more DSPs, general purpose microprocessors, ASICs, FPGAs, or other equivalent integrated or discrete logic circuitry. In this sense, the techniques are implemented in hardware, whether implemented entirely in hardware or in hardware such as a processor executing computer-readable code. Accordingly, the term "processor," as used herein may refer to any of the foregoing structure or any other structure suitable for implementation of the techniques described herein.

The invention claimed is:

1. A system comprising:
   a therapy module; and
   a processor configured to detect a voiding event of a patient and control the therapy module to deliver electrical stimulation to the patient at a first intensity level for a period of time in response to the detection of the voiding event, and immediately following the period of time, control the therapy module to increase intensity of the electrical stimulation from the first intensity level to a second intensity level before a subsequent voiding event of the patient by at least controlling the therapy module to deliver stimulation to the patient at a plurality of intermediate intensity levels between the first and second intensity levels prior to delivering stimulation to the patient at the second intensity level following the detection of the voiding event, wherein the first intensity level is selected to be an intensity of electrical stimulation applied to the patient that produces a delayed physiological response of the patient relative to the delivery of the electrical stimulation at the first intensity level, and the second intensity level is selected to be an intensity of electrical stimulation applied to the patient that produces the physiological response of the patient relative to the delivery of the electrical stimulation at the second intensity level in a shorter amount of time than the electrical stimulation at the first intensity level.

2. The system of claim 1, wherein the processor is configured to control the therapy module to increase intensity of the electrical stimulation from the first intensity level to the second intensity level by adjusting at least one of an amplitude of the electrical stimulation, a pulse rate of the electrical stimulation, or a pulse width of the electrical stimulation.

3. The system of claim 1, further comprising a sensor configured to generate a signal indicative of a patient parameter, wherein the processor is configured to detect the voiding event of the patient based on the signal generated by the sensor.

4. The system of claim 3, wherein the signal generated by the sensor indicates at least one of bladder impedance, bladder pressure, pudendal or sacral afferent nerve activity, muscle activity, or motion of the patient.

5. The system of claim 1, wherein the processor is configured to detect the voiding event of the patient based on patient input.

6. The system of claim 5, further comprising a programmer, wherein the processor is configured to receive the patient input via the programmer.

7. The system of claim 1, wherein the first intensity level is selected such that stimulation is not perceivable by the patient.

8. The system of claim 1, wherein the period of time is a predetermined period of time.

9. The system of claim 1, wherein the processor is configured to determine the period of time based on at least one of patient input or a signal received from a sensor.

10. The system of claim 9, wherein the at least one of the patient input or the signal received from the sensor is received by the processor prior to detection of the voiding event.

11. The system of claim 9, wherein the processor is configured to determine the period of time based on an amount of time between two voiding events that occurred prior to the detected voiding event.

12. The system of claim 1, wherein the processor is configured to control the therapy module to increase intensity of the electrical stimulation applied to the patient using at least one of a ramp function, one or more step functions, or a curvilinear function.

13. The system of claim 1, wherein the processor is configured to control the therapy module to gradually increase intensity of the electrical stimulation from the first intensity level to the second intensity level over a predetermined period of time.

14. The system of claim 1, wherein the processor is configured to control the therapy module to increase intensity of electrical stimulation from the first intensity level to the second intensity level during a transition period, wherein a duration of the transition period is based on input from at least one of the patient or a sensor that generates a signal indicative of a patient parameter.

15. The system of claim 14, wherein the at least one of the input from the patient or the sensor is received by the processor prior to detection of the voiding event.

16. The system of claim 1, wherein the processor is configured to detect the subsequent voiding event, and control the therapy module to decrease intensity of the electrical stimulation from the second intensity level to the first intensity level immediately after detection of the subsequent voiding event, wherein the therapy module is configured to deliver electrical stimulation to the patient at the first intensity level immediately following the subsequent voiding event, and wherein the therapy module is configured to, immediately following delivery of electrical stimulation at the first intensity level, increase intensity of the electrical stimulation from the first intensity level to the second intensity level.

17. The system of claim 1, wherein the processor is configured to control the therapy module to deliver electrical stimulation to the patient at the first intensity level according to a therapy program that defines a stimulation intensity that is less than a threshold stimulation intensity, wherein the threshold stimulation intensity is defined by a plurality of stimulation parameters and elicits a substantially acute physiological response in the patient indicative of electrical capture of a nerve.

18. The system of claim 1, wherein the processor is configured to, immediately following the voiding event, control the therapy module to deliver electrical stimulation to the patient at the first intensity level for the period of time.

19. The system of claim 1, wherein the second intensity level is selected to produce the physiological response of the patient substantially immediately upon delivery of the electrical stimulation at the second intensity level.

20. The system of claim 1, wherein the physiological response of the patient comprises a reduction in bladder contraction frequency.

21. The method of claim 1, wherein the physiological response of the patient comprises a reduction in bladder contraction frequency.

22. A method comprising:
    detecting a voiding event of a patient;
    with a processor, controlling a therapy module to deliver electrical stimulation to the patient at a first intensity level for a period of time in response to the detection of the voiding event, wherein the first intensity level is selected to be an intensity of electrical stimulation applied to the patient that produces a delayed physiological response of the patient relative to the delivery of the electrical stimulation at the first intensity level; and
    with the processor, immediately following the period of time, controlling the therapy module to increase intensity of the electrical stimulation from the first intensity level to a second intensity level before a subsequent voiding event of the patient, wherein the second intensity level is selected to be an intensity of electrical stimulation applied to the patient that produces the physiological response of the patient relative to the delivery of the electrical stimulation at the second intensity level in a shorter amount of time than the electrical stimulation at the first intensity level, and wherein increasing intensity of the electrical stimulation comprises delivering electrical stimulation to the patient at a plurality of intermediate intensity levels between the first and second intensity levels prior to delivering stimulation to the patient at the second intensity level following the detection of the voiding event.

23. The method of claim 22, further comprising increasing intensity of the electrical stimulation from the first intensity level to the second intensity level by adjusting at least one of an amplitude of the electrical stimulation, a pulse rate of the electrical stimulation, or a pulse width of the electrical stimulation.

24. The method of claim 22, further comprising detecting, with the processor, the voiding event of the patient based on at least one of patient input or a signal generated by a sensor, wherein the signal is indicative of at least one of bladder impedance, bladder pressure, pudendal or sacral afferent nerve activity, muscle activity, or motion of the patient.

25. The method of claim 22, wherein the first intensity level is selected such that stimulation is not perceivable by the patient.

26. The method of claim 22, further comprising determining, with the processor, the period of time based on one of a signal received from a sensor or patient input.

27. The method of claim 26, further comprising receiving the one of the signal received from the sensor or the patient input with the processor prior to detection of the voiding event.

28. The method of claim 26, further comprising determining, with the processor, the period of time based on an amount of time between two voiding events that occurred prior to the detected voiding event.

29. The method of claim 22, wherein controlling the therapy module to increase intensity of the electrical stimulation comprises controlling, with the processor, the therapy module to deliver stimulation to the patient according to at least one of a ramp function, one or more step functions, or a curvilinear function.

30. The method of claim 22, wherein controlling the therapy module to increase intensity of electrical stimulation comprises controlling, with the processor, the therapy module to increase intensity of the electrical stimulation from the first intensity level to the second intensity level during a transition period, wherein a duration of the transition period is based on input from at least one of the patient or a sensor that generates a signal indicative of a patient parameter.

31. The method of claim 30, wherein the input is received prior to detection of the voiding event.

32. The method of claim 22, further comprising:
    detecting the subsequent voiding event;
    with the processor, controlling the therapy module to decrease intensity of the electrical stimulation from the second intensity level to the first intensity level immediately after detecting the subsequent voiding event;
    with the processor, controlling the therapy module to deliver electrical stimulation to the patient at the first intensity level immediately following the subsequent voiding event; and
    with the processor, immediately following delivery of electrical stimulation at the first intensity level for the period of time, controlling the therapy module to increase intensity of the electrical stimulation from the first intensity level to the second intensity level.

33. The method of claim 22, wherein controlling the therapy module to deliver electrical stimulation to the patient at the first intensity level comprises controlling the therapy module to deliver electrical stimulation according to a therapy program that defines a stimulation intensity that is less than a threshold stimulation intensity, wherein the threshold stimulation intensity is defined by a plurality of stimulation parameters and elicits a substantially acute physiological response in the patient indicative of electrical capture of a nerve.

34. The method of claim 22, wherein the second intensity level is selected to produce the physiological response of the patient substantially immediately upon delivery of the electrical stimulation at the second intensity level.

35. A system comprising:
    means for detecting a voiding event of a patient;
    means for delivering electrical stimulation to the patient at a first intensity level for a period of time in response to the detection of the voiding event, wherein the first intensity level is selected to be an intensity of electrical stimulation applied to the patient that produces a delayed physiological response of the patient relative to the delivery of the electrical stimulation at the first intensity level; and
    means for controlling the means for delivering electrical stimulation to increase intensity of the electrical stimulation from the first intensity level to a second intensity level immediately following the period of time and before a subsequent voiding event of the patient, wherein the second intensity level is selected to be an intensity of electrical stimulation applied to the patient that produces the physiological response of the patient relative to the delivery of the electrical stimulation at the second intensity level in a shorter amount of time than the electrical stimulation at the first intensity level, wherein the means for controlling controls the means for delivering electrical stimulation to increase intensity of the electrical stimulation by at least delivering electrical stimulation to the patient at a plurality of intermediate intensity levels between the first and second intensity levels prior to delivering stimulation to the patient at the second intensity level following the detection of the voiding event.

36. The system of claim 35, further comprising means for detecting the voiding event of the patient based on at least one of patient input or a signal generated by a sensor.

37. The system of claim 35, wherein the period of time is a predetermined period of time.

38. The system of claim 35, further comprising means for determining the period of time based on one of a signal received from a sensor or patient input.

39. The system of claim 35, wherein the means for controlling controls the means for delivering electrical stimulation to increase intensity of the electrical stimulation according to at least one of a ramp function, one or more step functions, or a curvilinear function.

40. The system of claim 36, wherein the second intensity level is selected to produce the physiological response of the patient substantially immediately upon delivery of the electrical stimulation at the second intensity level.

41. A non-transitory computer-readable storage medium comprising instructions that cause a programmable processor to
    detect a voiding event of a patient;
    control a therapy module to deliver electrical stimulation to the patient at a first intensity level for a period of time in response to the detection of the voiding event, wherein the first intensity level is selected to be an intensity of electrical stimulation applied to the patient that produces a delayed physiological response of the patient relative to the delivery of the electrical stimulation at the first intensity level; and
    control the therapy module to increase intensity of the electrical stimulation from the first intensity level to a second intensity level immediately following the period of time and before a subsequent voiding event of the patient, wherein the second intensity level is selected to be an intensity of electrical stimulation applied to the patient that produces the physiological response of the patient relative to the delivery of the electrical stimulation at the second intensity level in a shorter amount of time than the electrical stimulation at the first intensity level, and wherein the instructions cause the processor to control the therapy module to increase intensity of the electrical stimulation by at least delivering electrical stimulation to the patient at a plurality of intermediate intensity levels between the first and second intensity levels prior to delivering stimulation to the patient at the second intensity level following the detection of the voiding event.

42. The computer-readable storage medium of claim 41, further comprising instructions that cause the programmable processor to detect the voiding event of the patient based on at least one of patient input or a signal generated by a sensor.

43. The computer-readable storage medium of claim 41, further comprising instructions that cause the programmable processor to determine the period of time based on one of a signal received from a sensor or patient input.

44. The computer-readable storage medium of claim 41, wherein the second intensity level is selected to produce the physiological response of the patient substantially immediately upon delivery of the electrical stimulation at the second intensity level.

* * * * *